US012653440B2

(12) United States Patent
Lei et al.

(10) Patent No.: US 12,653,440 B2
(45) Date of Patent: Jun. 16, 2026

(54) MOTOR IMAGERY ELECTROENCEPHALOGRAM SIGNAL PROCESSING METHOD, DEVICE, AND STORAGE MEDIUM

(71) Applicant: Tencent Technology (Shenzhen) Company Limited, Shenzhen (CN)

(72) Inventors: Mengying Lei, Shenzhen (CN); Zijun Deng, Shenzhen (CN); He Zhao, Shenzhen (CN); Qingqing Zheng, Shenzhen (CN); Kai Ma, Shenzhen (CN); Yefeng Zheng, Shenzhen (CN)

(73) Assignee: Tencent Technology (Shenzhen) Company Limited, Shenzhen (CN)

( * ) Notice: Subject to any disclaimer, the term of this patent is extended or adjusted under 35 U.S.C. 154(b) by 1225 days.

(21) Appl. No.: 17/516,427

(22) Filed: Nov. 1, 2021

(65) Prior Publication Data

US 2022/0054071 A1    Feb. 24, 2022

Related U.S. Application Data

(63) Continuation of application No. PCT/CN2020/112766, filed on Sep. 1, 2020.

(30) Foreign Application Priority Data

Sep. 6, 2019    (CN) .......................... 201910843985.7

(51) Int. Cl.
*A61B 5/375*         (2021.01)
*A61B 5/372*         (2021.01)
(Continued)

(52) U.S. Cl.
CPC .............. *A61B 5/375* (2021.01); *A61B 5/372* (2021.01); *G06F 18/22* (2023.01); *G06N 3/045* (2023.01);
(Continued)

(58) Field of Classification Search
CPC ..... A61B 5/375; A61B 5/372; A61B 2505/09; A61B 5/369; A61B 5/7267; A61B 5/72;
(Continued)

(56) References Cited

U.S. PATENT DOCUMENTS

2014/0277582 A1*   9/2014   Leuthardt .............. A61B 5/372
                                                                        623/25
2019/0209038 A1    7/2019   Saab et al.

FOREIGN PATENT DOCUMENTS

CN          104523268 A       4/2015
CN          105468143 A       4/2016
(Continued)

OTHER PUBLICATIONS

Extended European Search Report for corresponding application No. EP 208603753 dated Oct. 11, 2022, 11p.
(Continued)

*Primary Examiner* — Abid A Mustansir
(74) *Attorney, Agent, or Firm* — Crowell & Moring LLP

(57)                    ABSTRACT

This disclosure discloses a method and apparatus for processing a motor MI-EEG signal and a storage medium. The method includes: inputting a source MI-EEG signal belonging to a source domain and a target MI-EEG signal belonging to a target domain to an initial feature extraction model to obtain first source MI features and first target MI features; inputting the first source MI features to an initial classification model to obtain a first classification result outputted by the initial classification model, the first classification result representing an action predicted to be performed in the source MI-EEG signal; and adjusting a model parameter of the initial feature extraction model and/or a model parameter of the initial classification model when a certain condition (set) is met.

20 Claims, 7 Drawing Sheets

(51) Int. Cl.

| | | |
|---|---|---|
| *G06F 3/01* | (2006.01) |
| *G06F 18/22* | (2023.01) |
| *G06N 3/045* | (2023.01) |
| *G06V 10/40* | (2022.01) |
| *G16H 40/63* | (2018.01) |
| *G16H 50/20* | (2018.01) |

(52) U.S. Cl.
CPC .............. *G06V 10/40* (2022.01); *G16H 40/63* (2018.01); *G16H 50/20* (2018.01); *A61B 2505/09* (2013.01); *G06F 3/015* (2013.01)

(58) Field of Classification Search
CPC .... G06F 18/22; G06F 3/015; G06F 18/24143; G06F 2218/08; G06F 2218/12; G06N 3/045; G06N 3/044; G06N 3/088; G06V 10/40; G06V 10/454; G06V 40/15; G16H 40/63; G16H 50/20
See application file for complete search history.

(56) References Cited

FOREIGN PATENT DOCUMENTS

| | | |
|---|---|---|
| CN | 106108893 A | 11/2016 |
| CN | 106933353 A | 7/2017 |
| CN | 109583346 A | 4/2019 |
| CN | 109784211 A | 5/2019 |
| CN | 109992113 A | 7/2019 |
| CN | 110147878 A | 8/2019 |
| CN | 110531861 A | 12/2019 |
| WO | WO 2017/084416 A1 | 5/2017 |
| WO | WO 2021/043118 A1 | 3/2021 |

OTHER PUBLICATIONS

Jeon, Eunjin et al., "Domain Adaptation with Source Selection for Motor-Imagery based BCI", 7th International Winter Conference on Brain-computer Interface (BCI), IEEE, Feb. 18, 2019, 4p. KR.

Ozdenizci, Ozan et al., "Transfer Learning in Brain-Computer Interfaces with Adversarial Variational Autoencoders", 9th International EMBS Conference on Neural Engineering, IEEE, Mar. 23, 2019, 4p, US.

Luo, Yun et al., "WGAN Domain Adaption for EEG-Based Emotion Recognition", Lecture Notes, Springer Nature Switzerland AG, Nov. 17, 2018, pp. 275-286, CH.

Tan, Chuanqi et al., "Adaptive Adversarial Transfer Learning for Electroencephalography Classification", International Joint Conference on Neural Networks, IJCNN, IEEE, Jul. 8, 2018, 8p, CN.

Lotte, F. et al., "A review of classification algorithms for EEG-based brain-computer interfaces: a 10 year update", Institute of Physics Publishing, Journal of Neural Engineering, vol. 15, No. 3, Apr. 16, 2018, 28p, GB.

International Search Report and Written Opinion for priority application No. PCT/CN2020/112766 dated Dec. 9, 2020, 11p. in Chinese Language.

English language translation of the International Search Report for priority application No. PCT/CN2020/112766 dated Dec. 9, 2020, 2p.

Concise Explanation of Relevance for ref. A13, A16, A17, and A18.

China Patent Office Search Report for Chinese application No. 201910843985.7 dated May 19, 2021, 3p, in Chinese language.

First Office Action for Chinese application No. 201910843985.7 dated May 27, 2021, 10p, in Chinese language.

Han, Fei, "Research on Feature Extraction and Feature Transfer of EEG Based on Motor Imagery", *Medicine and Health Sciences*, Jun. 2017, 60 p, ISSN 1674-0246.

\* cited by examiner

Convolutional layer
(Time)
40 unit

Convolutional layer
(all electrodes/patches)
40 unit

Average pooling layer
Step size 15×1

Linear classification layer
(Compact layer + Softmax)
4 unit

Square

Log

Hand (left)   Hand (right)   Foot   Others

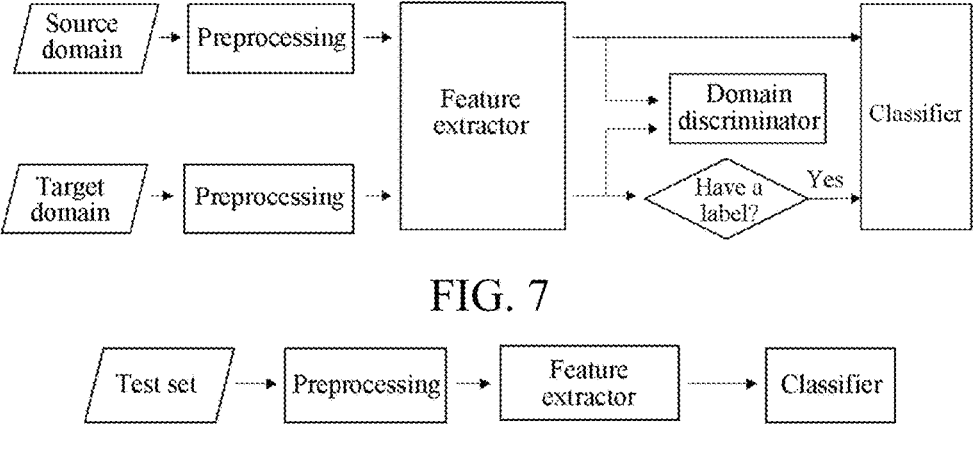

FIG. 7

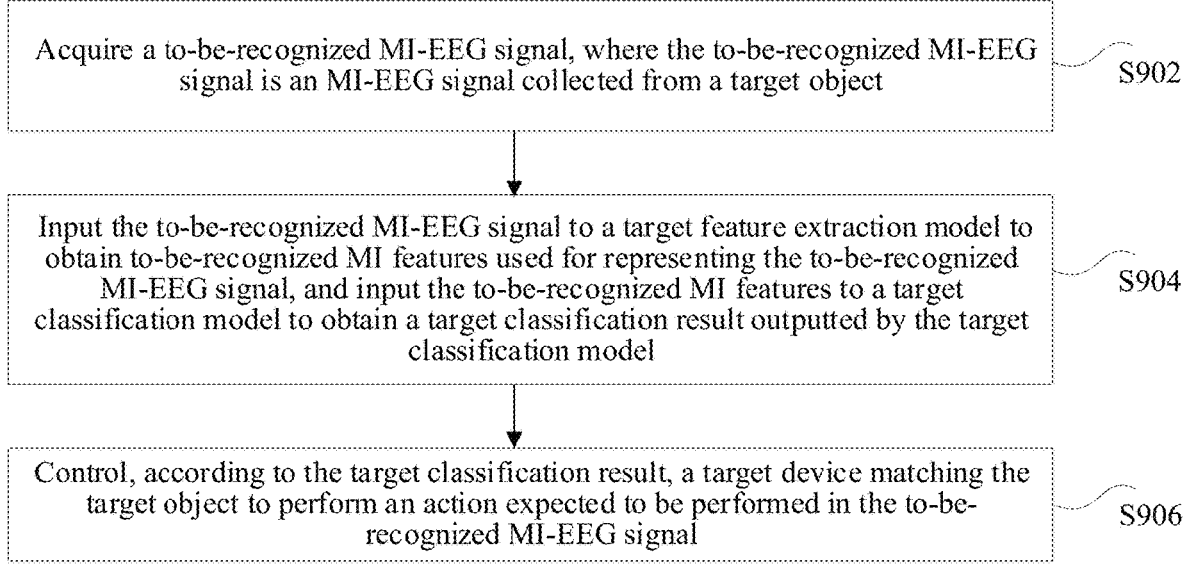

FIG. 8

| | |
|---|---|
| Acquire a to-be-recognized MI-EEG signal, where the to-be-recognized MI-EEG signal is an MI-EEG signal collected from a target object | S902 |
| Input the to-be-recognized MI-EEG signal to a target feature extraction model to obtain to-be-recognized MI features used for representing the to-be-recognized MI-EEG signal, and input the to-be-recognized MI features to a target classification model to obtain a target classification result outputted by the target classification model | S904 |
| Control, according to the target classification result, a target device matching the target object to perform an action expected to be performed in the to-be-recognized MI-EEG signal | S906 |

FIG. 9

MOTOR IMAGERY ELECTROENCEPHALOGRAM SIGNAL PROCESSING METHOD, DEVICE, AND STORAGE MEDIUM

RELATED APPLICATION

This application is a continuation of PCT Application No. PCT/CN2020/112766, filed Sep. 1, 2020 and entitled MOTOR IMAGERY ELECTROENCEPHALOGRAM SIGNAL PROCESSING METHOD, DEVICE, AND STORAGE MEDIUM, which claims priority to Chinese Patent Application No. 201910843985.7, filed with the China National Intellectual Property Administration, PRC on Sep. 6, 2019, entitled "METHOD AND APPARATUS FOR PROCESSING MOTOR IMAGERY ELECTROENCEPHALOGRAM SIGNAL, AND STORAGE MEDIUM." The above applications are incorporated herein by reference in their entireties.

TECHNICAL FIELD

This application relates to the field of artificial intelligence (AI), and specifically, to a technology for processing a motor imagery electroencephalogram (MI-EEG) signal.

BACKGROUND

A motor imagery-brain-computer interface (MI-BCI) is a man-machine interaction mode, which is to control movement of an external device through spontaneous imagery of limb movement. An MI-BCI-based system may be used to help patients with limb disabilities perform rehabilitation training, and control a machine to achieve self-care to improve living quality, and may also be used to enrich the life of general populations, for example, a brain-computer game.

At present, because MI-EEG signals vary greatly among individuals, and models of different subjects cannot be shared, the MI-BCI system needs to train one independent model for an EEG signal of each subject, and recognize the EEG signal of the subject by using the model obtained through training.

Performance of the MI-BCI system obtained by using the above method is affected by decoding accuracy of the MI-EEG signal to a great extent. In addition, the MI-BCI system cannot be applied to untrained subjects, and therefore each subject needs to be trained before actual use of the MI-BCI system. Because the training process is cumbersome and complex and a quantity of training samples of each subject is small, the performance of the system is further degraded.

Therefore, there is a problem of low accuracy of decoding MI-EEG signals of different objects by an MI recognition model due to the MI-EEG signals varying greatly among subject individuals in the related art.

SUMMARY

Embodiments of this disclosure provide a method and apparatus for processing an MI-EEG signal and a storage medium, so as to resolve at least the technical problem of low accuracy of decoding MI-EEG signals of different objects by an MI recognition model due to the MI-EEG signals varying greatly among subject individuals in the related art.

According to an aspect of the embodiments of this disclosure, a method for processing an MI-EEG signal is provided, including: inputting a source MI-EEG signal belonging to a source domain and a target MI-EEG signal belonging to a target domain to an initial feature extraction model to obtain first source MI features representing the source MI-EEG signal and first target MI features representing the target MI-EEG signal;

inputting the first source MI features to an initial classification model to obtain a first classification result outputted by the initial classification model, the first classification result representing an action predicted to be performed in the source MI-EEG signal; and adjusting a model parameter of the initial feature extraction model and/or a model parameter of the initial classification model to obtain a target feature extraction model and a target classification model when a first known action corresponding to the source MI-EEG signal is inconsistent with the action predicted to be performed of the source MI-EEG signal, or a similarity between a feature distribution of the first source MI features and a feature distribution of the first target MI features is less than a first predetermined threshold, wherein a similarity between a feature distribution of second source MI features representing the source MI-EEG signal that are outputted by the target feature extraction model and a feature distribution of second target MI features representing the target MI-EEG signal that are outputted by the target feature extraction model is greater than or equal to the first predetermined threshold, and an action predicted to be performed, represented by a second classification result outputted by the target classification model, of the source MI-EEG signal that is consistent with the first known action.

According to another aspect of the embodiments of this disclosure, a method for processing an MI-EEG signal is provided, including: acquiring a to-be-recognized MI-EEG signal, the to-be-recognized MI-EEG signal being an MI-EEG signal collected from a target object; inputting the to-be-recognized MI-EEG signal to a target feature extraction model, to obtain to-be-recognized MI features used for representing the to-be-recognized MI-EGG signal, and inputting the to-be-recognized MI features to a target classification model, to obtain a target classification result outputted by the target classification model, a similarity between feature distributions of different MI features and the to-be-recognized MI features extracted by the target feature extraction model for different MI training signals being greater than or equal to a first similarity threshold, the different MI training signals including a target MI-EEG signal and a source MI-EEG signal corresponding to a first known action, an action predicted to be performed in the source MI-EEG signal that is represented by a classification result outputted by the target classification model being consistent with the first known action, the classification result being a classification result determined by the target classification model according to source MI features extracted from the source MI-EEG signal by the target feature extraction model, and the target classification result being used for representing an action predicted to be performed in the to-be-recognized MI-EEG signal; and controlling, according to the target classification result, a target device matching the target object to perform the action predicted to be performed in the to-be-recognized MI-EEG signal.

According to still another aspect of the embodiments of this disclosure, an apparatus for processing an MI-EEG signal is further provided, including: a first input unit, configured to input a source MI-EEG signal belonging to a source domain and a target MI-EEG signal belonging to a target domain to an initial feature extraction model, to obtain first source MI features used for representing the source MI-EEG signal and first target MI features used for representing the target MI-EEG signal; a second input unit, configured to input the first source MI features to an initial classification model, to obtain a first classification result outputted by the initial classification model, the first classification result being used for representing an action predicted to be performed in the source MI-EEG signal; and an adjustment unit, configured to adjust a model parameter of the initial feature extraction model and/or a model parameter of the initial classification model when a first known action corresponding to the source MI-EEG signal is inconsistent with the action predicted to be performed, represented by the first classification result, of the source MI-EEG signal, or a similarity between a feature distribution of the first source MI features and a feature distribution of the first target MI features is less than a first predetermined threshold, to obtain a target feature extraction model and a target classification model, a similarity between a feature distribution of second source MI features used for representing the source MI-EEG signal that are outputted by the target feature extraction model and a feature distribution of second target MI features used for representing the target MI-EEG signal that are outputted by the target feature extraction model being greater than or equal to the first predetermined threshold, and an action predicted to be performed in the source MI-EEG signal that is represented by a second classification result outputted by the target classification model being consistent with the first known action.

According to still another aspect of the embodiments of this disclosure, an apparatus for processing an MI-EEG signal is further provided, including: a second acquisition unit, configured to acquire a to-be-recognized MI-EEG signal, the to-be-recognized MI-EEG signal being an MI-EEG signal collected from a target object; a fourth input unit, configured to successively input the to-be-recognized MI-EEG signal to a target feature extraction model, to obtain to-be-recognized MI features used for representing the to-be-recognized MI-EGG signal, and output the to-be-recognized MI features to a target classification model, to obtain a target classification result inputted by the target classification model, a similarity between different MI features extracted by the target feature extraction model for different MI training signals being greater than or equal to a first similarity threshold, the different MI training signals including a target MI-EEG signal and a source MI-EEG signal corresponding to a first known action, an action predicted to be performed in the source MI-EEG signal that is represented by a classification result outputted by the target classification model being consistent with the first known action, the classification result being a classification result determined by the target classification model according to source MI features extracted from the source MI-EEG signal by the target feature extraction model, and the target classification result being used for representing an action predicted to be performed in the to-be-recognized MI-EEG signal; and a control unit, configured to control, according to the target classification result, a target device matching the target object to perform the action predicted to be performed in the to-be-recognized MI-EEG signal.

According to still another aspect of the embodiments of this disclosure, a non-transitory computer-readable storage medium is further provided, storing a computer program, the computer program being configured to, when run, cause an electronic device to perform the methods disclosed herein.

According to still another aspect of the embodiments of this disclosure, an electronic device is further provided, including a memory and a processor, the memory storing a computer program, and the processor being configured to execute the computer program to cause the electronic device to perform the steps, comprising:

inputting a source MI-EEG signal belonging to a source domain and a target MI-EEG signal belonging to a target domain to an initial feature extraction model to obtain first source MI features representing the source MI-EEG signal and first target MI features representing the target MI-EEG signal;

inputting the first source MI features to an initial classification model to obtain a first classification result outputted by the initial classification model, the first classification result representing an action predicted to be performed in the source MI-EEG signal; and adjusting a model parameter of the initial feature extraction model and/or a model parameter of the initial classification model to obtain a target feature extraction model and a target classification model when a first known action corresponding to the source MI-EEG signal is inconsistent with the action predicted to be performed of the source MI-EEG signal, or a similarity between a feature distribution of the first source MI features and a feature distribution of the first target MI features is less than a first predetermined threshold, wherein a similarity between a feature distribution of second source MI features representing the source MI-EEG signal that are outputted by the target feature extraction model and a feature distribution of second target MI features representing the target MI-EEG signal that are outputted by the target feature extraction model is greater than or equal to the first predetermined threshold, and an action predicted to be performed, represented by a second classification result outputted by the target classification model, of the source MI-EEG signal that is consistent with the first known action.

According to still another aspect of the embodiments of this disclosure, a computer program product is further provided, the computer program product, when run on a computer, causing the computer to perform the above method.

In the embodiments of this disclosure, the feature extraction model and the classification model are trained by using the source MI-EEG signal corresponding to the first known action and the target MI-EEG signal, so that the features of the source MI-EEG signal and the features of the target MI-EEG signal that are extracted by the feature extraction model are distributed in a similar manner, and the classification model can correctly recognize the first known action. Because the features of the target MI-EEG signal and the source MI-EGG signal are distributed in a similar manner, the target feature extraction model and the target classification model obtained may be applicable to recognition of the MI-EEG signals of the target object, so as to improve the generalization capability of the MI recognition model (including the feature extraction model and the classification model obtained) and the accuracy of decoding (classification), thereby resolving the technical problem of low accuracy of decoding MI-EEG signals of different objects by an MI recognition model due to the MI-EEG signals varying greatly among subject individuals in the related art.

BRIEF DESCRIPTION OF THE DRAWINGS

FIG. 7 is a schematic flowchart of another optional method for processing an MI-EEG signal according to an embodiment of this disclosure.

FIG. 8 is a schematic flowchart of still another optional method for processing an MI-EEG signal according to an embodiment of this disclosure.

FIG. 9 is a schematic flowchart of yet still another optional method for processing an MI-EEG signal according to an embodiment of this disclosure.

DESCRIPTION OF EMBODIMENTS

Technical terms involved in embodiments of this disclosure include the following:

(1) A BCI refers to a channel mode of exchanging information between a brain of a human or an animal and an external machine.

(2) An EEG (Electroencephalogram) refers to a curve graph obtained by collecting biological voltages of the brain in the scalp by using a non-invasive brain-computer interface device and magnifying for recording.

(3) MI refers to imagining limb movement in mind without any limb movement, which creates spontaneous EEG.

(4) A convolutional neural network (CNN) is a feedforward neural network that contains convolution calculation and has a deep structure, which is one of representative algorithms of deep learning.

(5) Transfer learning is to store a solution model of existing problems, and apply the model to other related but different problems.

(6) Domain adaptation is intended to cause a source domain to be generalized to a target domain with different data distributions by using a model obtained through supervised learning. Data of the source domain and the target domain is mapped to one feature space, so that the data is distributed close to each other in the space as far as possible, thereby improving the processing performance of the model in the target domain.

(7) A generative adversarial network (GAN) is used to cause, through unsupervised learning, a generator and a discriminator of two neural networks to contest with each other for learning.

(8) A maximum mean discrepancy (discrepancy measure) is used to measure a similarity between two distributions.

Figure 1:
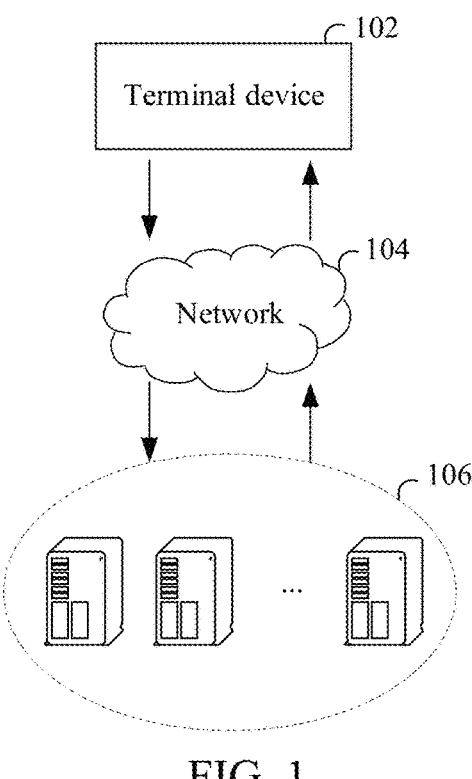
FIG. 1 is a schematic diagram of an application environment of a method for processing an MI-EEG signal according to an embodiment of this disclosure.

According to an aspect of the embodiments of this disclosure, a method for processing a MI-EEG signal is provided. Exemplarily, the method for processing an MI-EEG signal may be applied to, but is not limited to, an application environment shown in FIG. 1. As shown in FIG. 1, the method for processing an MI-EEG signal involves interaction between a terminal device 102 and a server 106 by using a network 104.

The terminal device 102 may collect or acquire a source MI-EEG signal and a target MI-EEG signal from other devices, and transmit the acquired source MI-EEG signal and target MI-EEG signal to the server 106 by using the network 104. The source MI-EEG signal and the target MI-EEG signal may be MI-EEG signals belonging to different objects (subjects), and the source MI-EEG signal corresponds to a first known action. The source MI-EEG signal belongs to a source domain, and the target MI-EEG signal belongs to a target domain. The source domain includes the MI-EEG signal corresponding to a determined known action, and the target domain may include the MI-EEG signal corresponding to an undetermined known action.

After the server 106 acquires the above source MI-EEG signal and the target MI-EEG signal, the source MI-EEG signal and the target MI-EEG signal may be inputted to an initial feature extraction model, to obtain first source MI features used for representing the source MI-EEG signal and first target MI features used for representing the target MI-EEG signal. The first source MI features are inputted to an initial classification model to obtain a first classification result outputted by the initial classification model. The first classification result is used for representing an action predicted to be performed in the source MI-EEG signal. When a first known action corresponding to the source MI-EEG signal is inconsistent with the action predicted to be performed, represented by the first classification result, of the source MI-EEG signal, or a similarity between a feature distribution of the first source MI features and a feature distribution of the first target MI features is less than a first predetermined threshold, a model parameter of the initial feature extraction model and/or a model parameter of the initial classification model are/is adjusted to obtain a target feature extraction model and a target classification model. In this way, a similarity between a feature distribution of second source MI features used for representing the source MI-EEG signal that are outputted by the target feature extraction model and a feature distribution of second target MI features used for representing the target MI-EEG signal that are outputted by the target feature extraction model is greater than or equal to the first predetermined threshold, and an action predicted to be performed in the source MI-EEG signal that is represented by a second classification result outputted by the target classification model is consistent with the first known action corresponding to the source MI-EEG signal.

Exemplarily, the target feature extraction model and the target classification model may serve as a feature extractor and a classifier of an MI recognition model, and may further test the MI recognition model by using a test sample in a test set to determine the performance of the model, or may be used to acquire a to-be-recognized MI-EEG signal, recognize an action predicted to be performed in the to-be-recognized MI-EEG signal, and control a specific device to perform the action predicted to be performed in the to-be-recognized MI-EEG signal.

Exemplarily, in this embodiment, the above terminal device may include, but is not limited to, at least one of the following: a signal collection device configured to collect the MI-EEG signal, and the like. The foregoing network may include, but is not limited to, at least one of the following: a wireless network and a wired network. The wireless network includes: Bluetooth, Wi-Fi, and another network implementing wireless communication, and the wired network may include: a local area network, a metropolitan area network, and a wide area network. The above server may include, but is not limited to, at least one of the following: a server configured to train the MI recognition model. The foregoing description is merely an example, and is not limited in this embodiment.

Figure 2:
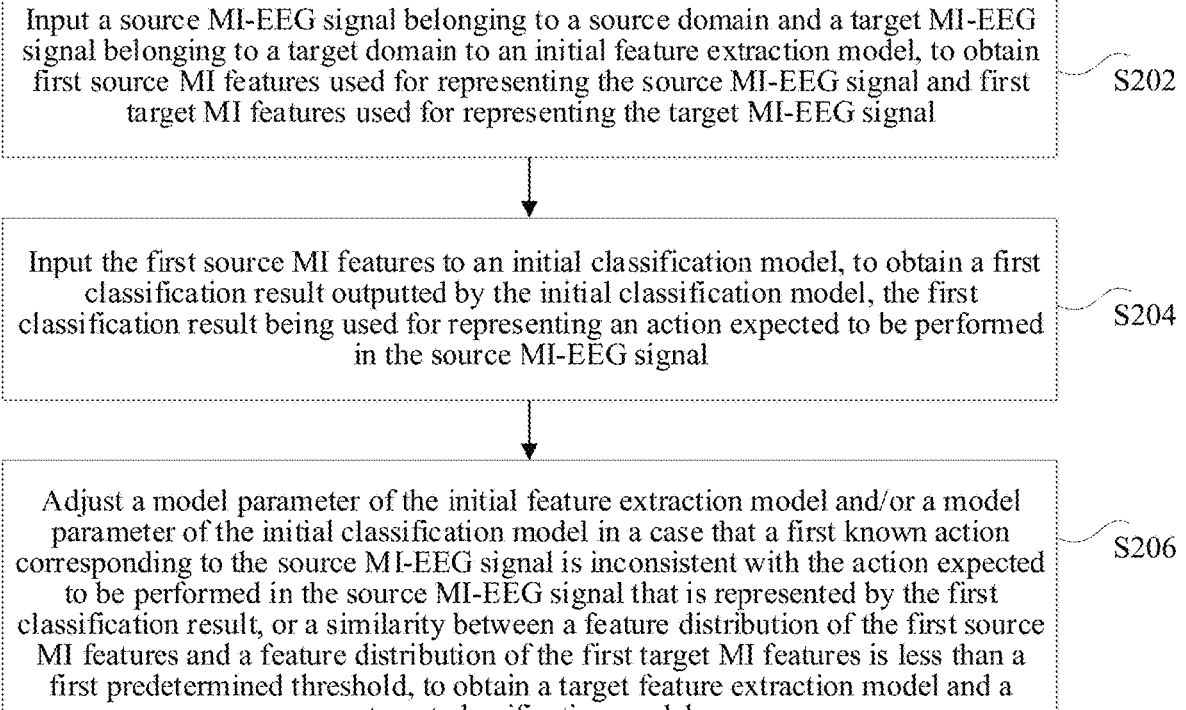
FIG. 2 is a schematic flowchart of an optional method for processing an MI-EEG signal according to an embodiment of this disclosure.

Exemplarily, in this embodiment, as an exemplary implementation, as shown in FIG. 2, the method for processing an MI-EEG signal may include the following steps.

Step S202: Input a source MI-EEG signal belonging to a source domain and a target MI-EEG signal belonging to a target domain to an initial feature extraction model to obtain first source MI features used for representing the source MI-EEG signal and first target MI features used for representing the target MI-EEG signal.

Step S204: Input the first source MI features to an initial classification model to obtain a first classification result outputted by the initial classification model, the first classification result being used for representing an action predicted to be performed in the source MI-EEG signal.

Step S206: Adjust a model parameter of the initial feature extraction model and/or a model parameter of the initial classification model when a first known action corresponding to the source MI-EEG signal is inconsistent with the action predicted to be performed, represented by the first classification result, of the source MI-EEG signal, or a similarity between a feature distribution of the first source MI features and a feature distribution of the first target MI features is less than a first predetermined threshold to obtain a target feature extraction model and a target classification model, wherein a similarity between a feature distribution of second source MI features used for representing the source MI-EEG signal that are outputted by the target feature extraction model and a feature distribution of second target MI features used for representing the target MI-EEG signal that are outputted by the target feature extraction model is greater than or equal to the first predetermined threshold, and an action predicted to be performed, represented by a second classification result, of the source MI-EEG signal outputted by the target classification model being consistent with the first known action.

Exemplarily, the target feature extraction model and the target classification model obtained by the method for processing an MI-EEG signal may serve as an MI recognition model. The MI recognition model may be applied to, but is not limited to, the process of transmission and control of ideas. For example, a BCI system combined with an exoskeleton robot can be used for active rehabilitation of motor functions of patients with hemiplegia or cerebral stroke, a BCI system combined with an electric wheelchair can help users with physical disabilities to travel freely, and a brain-computer-game system combined with a game can achieve activities of objects (including, but not limited to, at least one of the following: characters, articles, and the like) in a virtual world controlled by a human body through ideas and imagination.

Figure 3:
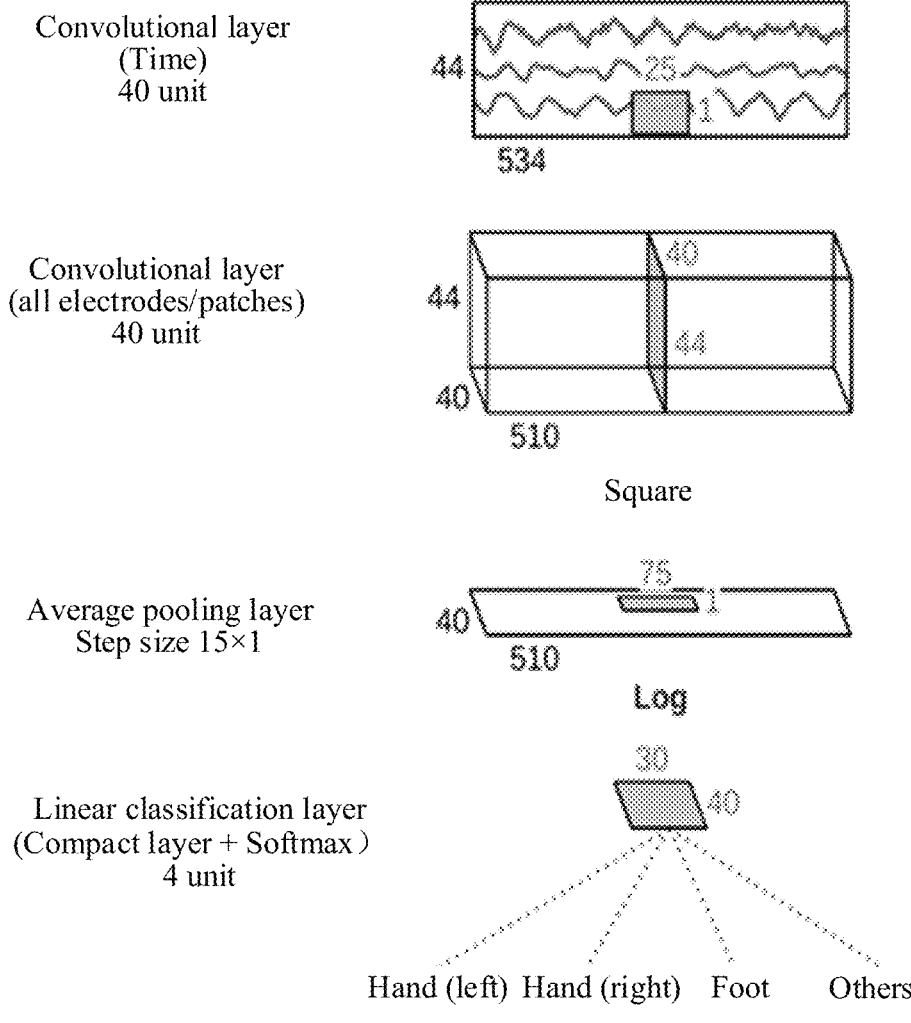
FIG. 3 is a schematic diagram of an optional method for processing an MI-EEG signal according to an embodiment of this disclosure.
Figure 4:
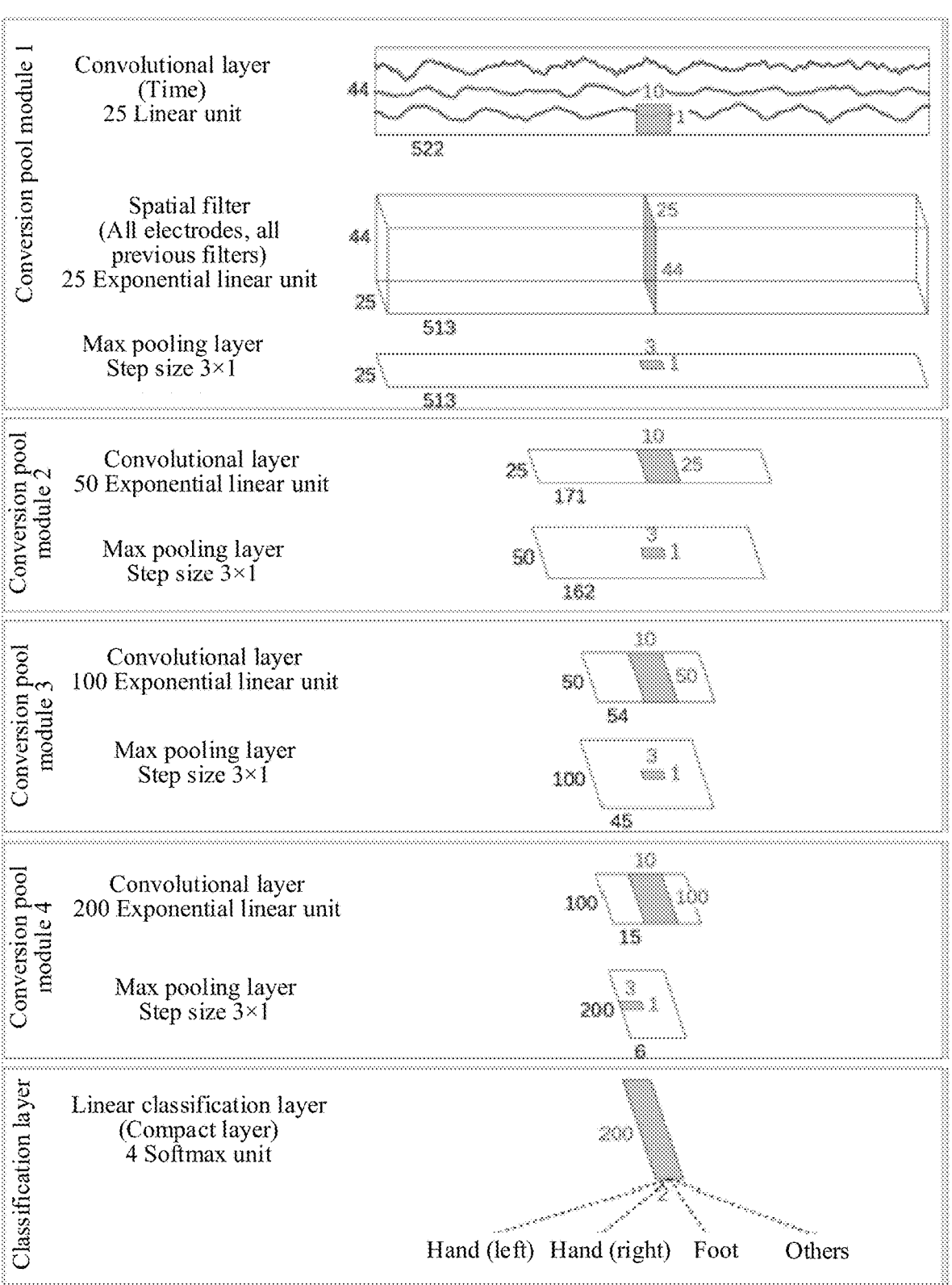
FIG. 4 is a schematic diagram of another optional method for processing an MI-EEG signal according to an embodiment of this disclosure.

The MI recognition modes in the related art may include a mode of an MI-EEG classification algorithm based on a shallow convolutional network (Shallow ConvNet) and a mode of an MI-EEG classification algorithm based on a deep convolutional network (Deep ConvNet). As shown in FIG. 3, an original EEG signal is used as a network input in the MI classification of the Shallow ConvNet, combining with characteristics of high temporal resolution and rich spatial information of the EEG signal, using a spatiotemporal mode of extracting the EEG signal through one-dimensional convolution of time and space, and through average pooling, full connectivity, and softmax, a classification probability corresponding to the signal is obtained. As shown in FIG. 4, a deep network structure of the Deep ConvNet is based on a shallow spatiotemporal convolution structure, and a plurality of convolutional pooling layers are increased in time dimension, to use EEG time information.

For the EEG classification algorithm based on the Shallow ConvNet, because the model structure is simple, extracted feature information is limited and is not enough to fit complex MI-EEG signals. The deep network based on the Deep ConvNet directly expands the Shallow ConvNet by increasing quantities of convolutional layers and pooling layers, and the training process requires more training samples, otherwise severe overfitting may be caused, resulting in poor generalization capability of the model.

Although the EEG classification methods based on the Shallow ConvNet and the Deep ConvNet both achieve end-to-end automatic recognition and decoding for EEG signals, due to large differences in signal of different subjects, the algorithms of the two network structures can only be trained independently for the training samples of different subjects, so that the models trained for different subjects cannot learn from each other, resulting in poor general transference of the models. In addition, the two algorithms both are supervised learning methods and cannot train and recognize the MI-EEG signals of unlabeled target subjects.

In this way, the feature extraction model and the classification model are trained by using the source MI-EEG signal corresponding to the first known action and the target MI-EEG signal, so that the features of the source MI-EEG signal and the features of the target MI-EEG signal that are extracted by the feature extraction model are distributed in a similar manner, and the classification model can correctly recognize the first known action, which mitigates the technical problem of low accuracy of decoding MI-EEG signals of different objects by an MI recognition model due to the MI-EEG signals varying greatly among subject individuals in the related art, and improves the generalization capability of the MI recognition model (including the obtained feature extraction model and classification model) and the accuracy of decoding.

The method for processing an MI-EEG signal is described below with reference to FIG. 2.

In step S202, the source MI-EEG signal belonging to the source domain and the target MI-EEG signal belonging to the target domain are inputted to the initial feature extraction model, to obtain the first source MI features used for representing the source MI-EEG signal and the first target MI features used for representing the target MI-EEG signal.

The MI recognition model used to recognize the MI-EEG signal may include a feature extraction model (a feature extractor) and a classification model (a classifier). In order to obtain the MI recognition model, subject training data (training data of subjects) may be used for model training. Training the MI recognition model may include a process of adjusting a model parameter of an initial feature extraction model and/or a model parameter of an initial classification model.

The training data of different subjects may be distributed to the source domain and the target domain. For example, an EEG signal of a target subject is assigned to the target domain, and the EEG signals of other subjects with high decoding performance are assigned to the source domain. The target MI-EEG signal in the target domain may or may not have a classification label. The source MI-EEG signal in the source domain has a classification label, the classification label may be used to identify the first known action corresponding to the source MI-EEG signal, and the first known action may be one of a plurality of known actions.

For example, in the training process, MI-EEG samples of different subjects may be distributed to the source domain and the target domain. The distribution may be performed according to specific problems. If there is data with no label in a subject data set, subject data with labels may be assigned to the source domain, and subject data with no label may be assigned to the target domain. If all subject data has labels, subject data of any one of subjects may be specified to be assigned to the target domain, and subject data of other subjects are assigned to the source domain, which may be repeated until all subject data of the subjects has ever been assigned to the target domain.

A plurality of known actions may be set according to experience, including, but not limited to, at least one of the following: a left-hand action (for example, clenching a left hand), a right-hand action (for example, clenching a right hand), a tongue action, a two-foot action (a left-foot action and a right-foot action may or may not be distinguished), and the like. Different classification labels may correspond to one of a plurality of known actions, and the same MI-EEG signal may correspond to one known action. Different MI-EEG signals may correspond to the same known action or may correspond to different known actions.

Exemplarily, in this embodiment, before the source MI-EEG signal belonging to the source domain and the target MI-EEG signal belonging to the target domain are inputted to the initial feature extraction model, the server may transmit a target instruction to the collection device, where the target instruction is used for indicating the first known action to be performed, and receive the source MI-EEG signal transmitted from the collection device, where the source MI-EEG signal is an MI-EEG signal collected by the collection device within a particular time period after receiving the target instruction.

In order to acquire the source MI-EEG signal, the server may transmit the target instruction to the collection device (an MI-EEG signal collection device), and the target instruction is used for indicating the first known action to be performed.

According to relevant protocol standards, an EEG signal of a specific object (for example, a human) may be collected at a predetermined location. There may be a plurality of (for example, 60) predetermined locations, which are distributed at different locations of a human head, and each location corresponds to a channel. A plurality of patches configured to collect EEG signals may be connected to the collection device, and different patches are configured to collect EEG signals of different channels.

The patches on the collection device may correspond to all or part of locations in the relevant protocol. The locations of the patches for collecting the EEG signals and a quantity of the patches may be set as required, which is not specifically limited in this embodiment.

For example, the protocol stipulates that there are N locations of the human head at which EEG signals are collected, which correspond to N different channels. EEG signals of all the N or a specific quantity of channels may be collected, or EEG signals of all the channels or only EEG signals of specific channels may be used during the processing.

After receiving the target instruction, the collection device may prompt the subject using the collection device with the first known action, and prompt the subject to imagine the first known action in mind, so as to collect the EEG signal of the subject, to obtain the source MI-EEG signal. The collection device may collect the MI-EEG signals (including the EEG signals of different channels) within a particular time period after receiving the target instruction.

The particular time period may be a time period during which the subject is required to be in an MI state after a first moment at which the target instruction is received, for example, 1 s (second) to 5.5 s after the first moment. Alternatively, the particular time period may be a particular time period during which the subject is in an MI state after a second moment at which a prompt message (for prompting the subject to imagine the first known action) is sent after the target instruction is received, for example, 1 s to 5.5 s after the second moment.

In this way, the collection device is instructed to collect MI-EEG signals by using the target instruction used for indicating the to-be-performed first known action, so that the source MI-EEG signal corresponding to the first known action may be obtained, so as to guarantee the accuracy of acquiring the source MI-EEG signal.

The target MI-EEG signal may be acquired by using the same method as the source MI-EEG signal (the target MI-EEG signal corresponding to a second known action), or may be acquired by using different methods. For example, the target instruction does not indicate a specific known action, and the subject needs to spontaneously imagine one of a plurality of known actions to acquire the target MI-EEG signal.

Exemplarily, in this embodiment, in order to improve the efficiency of acquiring training samples (the source MI-EEG signal and the target MI-EEG signal), a public data set may be used as training data. The labeled MI training data set may be used as the source domain, the unlabeled MI training data set may be used as the target domain, and MI-EEG signals of on-line unknown users may be used as the test set. The above public data set may be public competition data, for example, public MI data for the $3^{rd}$ China BCI competition.

Exemplarily, in this embodiment, before the source MI-EEG signal belonging to the source domain and the target MI-EEG signal belonging to the target domain are inputted to the initial feature extraction model, an initial source MI-EEG signal belonging to the source domain and an initial target MI-EEG signal belonging to the target domain may be acquired; the initial source MI-EEG signal is preprocessed to obtain the source MI-EEG signal; and the initial target MI-EEG signal is preprocessed to obtain the target MI-EEG signal.

The source MI-EEG signal and the target MI-EEG signal may be acquired by using the foregoing method, or the initial source MI-EEG signal and the initial target MI-EEG signal may be acquired by using the foregoing method. The initial source MI-EEG signal and the initial target MI-EEG signal are preprocessed to obtain the source MI-EEG signal and the target MI-EEG signal. The preprocessing of the MI-EEG signal may be used to standardize the MI-EEG signal, so that the preprocessed MI-EEG signal may be used for training an MI-EEG signal recognition model.

In this way, the initial source MI-EEG signal and the initial target MI-EEG signal are preprocessed, so that the MI-EEG signal can be optimized, and the effectiveness of training the MI-EEG signal recognition model can be improved.

As an exemplary implementation, the preprocessing the initial source MI-EEG signal to obtain the source MI-EEG signal includes: intercepting a signal of a predetermined duration from the initial source MI-EEG signal, to obtain a first source MI-EEG signal; inputting the first source MI-EEG signal to a band-pass filter, to obtain a second source MI-EEG signal, the band-pass filter being configured to filter out, from the first source MI-EEG signal, a signal not in a band-pass frequency band range; and standardizing the second source MI-EEG signal to obtain the source MI-EEG signal.

As another exemplary implementation, the preprocessing the initial target MI-EEG signal to obtain the target MI-EEG signal includes: intercepting a signal of a predetermined duration from the initial target MI-EEG signal, to obtain a first target MI-EEG signal; inputting the first target MI-EEG signal to a band-pass filter, to obtain a second target MI-EEG signal, the band-pass filter being configured to filter out, from the first target MI-EEG signal, a signal not in a band-pass frequency band range; and standardizing the second target MI-EEG signal to obtain the target MI-EEG signal.

The preprocessing of the MI-EEG signal (the MI-EEG signal may include the initial source MI-EEG signal and/or the initial target MI-EEG signal) may include, but is not limited to, at least one of the following: duration normalization, selection of a specific channel, denoising (low-pass filtering or band-pass filtering), and signal standardization.

Figure 5:
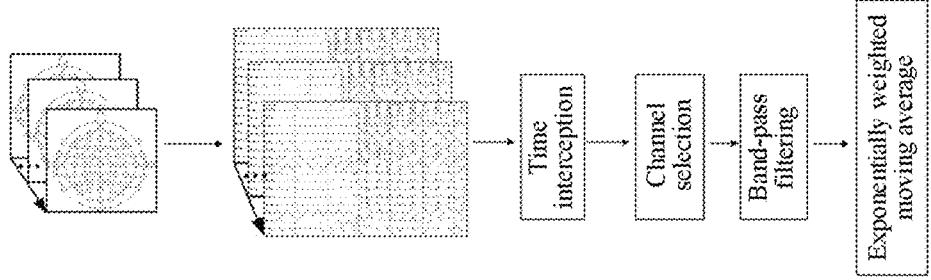
FIG. 5 is a schematic diagram of still another optional method for processing an MI-EEG signal according to an embodiment of this disclosure.

The preprocessing process of MI-EEG signals is described below in combination with optional examples. As shown in FIG. 5, the preprocessing operation for the MI-EEG signal may include, but is not limited to, at least one of the following steps.

1) Intercept Time Period Signals Related to MI (Duration Normalization)

Signals within an MI interval are intercepted for each sample, and data for a total of 4.5 s from 1 s to 5.5 s may be intercepted. Because a signal sampling frequency is 1000 Hz, a time dimension of each sample is 4500.

2) Channel Selection

Channel signals that are not related to MI tasks may be removed by means of channel selection. The selected channels may be 20 channels related to MI tasks (respectively FCz, FC1, FC2, FC3, FC4, FC5, FC6, Cz, C1, C2, C3, C4, C5, C6, CP1, CP2, CP3, CP4, CP5, and CP6), or may be more, less, or different channels.

3) Filtering

The noise introduced due to blinking, an environmental noise, and equipment, and the like may be removed by the band-pass filtering process. The band-pass filter may be a third-order Butterworth filter, and the band-pass range of the filter is [4-38 Hz] or may be [7-30 Hz]. Since useful information in the MI-EEG signal is mainly concentrated in a low-frequency region, the useful information in the MI-EEG signal may be retained while filtering out the noise by using the band-pass filter.

4) Exponentially Weighted Moving Average

For signals after smoothing filtering (signals after band-pass filtering), in order to further reduce signal fluctuation caused by noise, the exponentially weighted moving average operation may be used for standardizing the signal.

The signal standardization uses the exponentially weighted moving average method, and a weight parameter may be set to 0.999, or other standardization operations may be used, such as mean variance standardization, or a CSP algorithm.

In this way, the initial MI-EEG signal is preprocessed to filter out noise data, and lengths of the MI-EEG signals are unified and the MI-EEG signals are standardized, so as to improve the effectiveness of training the MI-EEG signal recognition model.

The source MI-EEG signal and the target MI-EEG signal may be inputted to the initial feature extraction model after being obtained, to obtain the first source MI features used for representing the source MI-EEG signal and the first target MI features used for representing the target MI-EEG signal.

The above initial feature extraction model may be a feature extractor that processes EEG signals based on the CNN, or may be a feature extractor having other network structures (such as ResNet and LSTM).

In step S204, the first source MI features are inputted to the initial classification model, to obtain the first classification result outputted by the initial classification model, the first classification result being used for representing the action predicted to be performed in the source MI-EEG signal.

The first source MI features extracted by the initial feature extraction model may be inputted to the initial classification model to obtain the first classification result outputted by the initial classification model that is used for representing the action predicted to be performed in the source MI-EEG signal. The initial classification model may be a classifier that processes EEG signals based on the CNN, and the classification result may be the action (corresponding to the known action having the highest probability) predicted to be performed in the source MI-EEG signal determined according to a probability of each known action predicted to be performed in the source MI-EEG signal determined by the first source MI features.

The feature extraction model and the classification model may be different submodels of the MI-EEG signal recognition model. The structures of the feature extraction model and the classification model may be pre-configured. The model parameter of the initial feature extraction model and the model parameter of the initial classification model may be model parameters that are randomly initialized (for example, initialized to 0), or may be model parameters obtained by training a randomly initialized initial feature extraction model and initial classification model by using the source MI-EEG signal.

For example, for the spatiotemporal attribute of the EEG signal, the feature extractor may adopt a temporal convolutional layer and a spatial convolutional layer. Based on the Deep ConvNet, the model parameters of the feature extractor and the classifier may be shown in Table 1. The network structure may be implemented by modifying a quantity of convolutional pooling layers and different convolution kernel sizes.

TABLE 1

| Layer name | Output size | Network |
|---|---|---|
| Output layer | 20 × 4500 | — |
| Temporal convolutional layer | 20 × 4491 | 1 × 10, 25, stride 1 × 1 |
| Spatial convolutional layer | 1 × 4491 | 20 × 1, 25, stride 1 × 1 |
| Max pooling layer | 1 × 1497 | 1 × 3, stride 1 × 3 |
| Convolutional layer 2 | 1 × 1488 | 1 × 10, 50, stride 1 × 1 |
| Max pooling layer | 1 × 496 | 1 × 3, stride 1 × 3 |
| Convolutional layer 3 | 1 × 487 | 1 × 10, 100, stride 1 × 1 |
| Max pooling layer | 1 × 162 | 1 × 3, stride 1 × 3 |
| Convolutional layer 4 | 1 × 153 | 1 × 10, 200, stride 1 × 1 |
| Max pooling layer | 1 × 51 | 1 × 3, stride 1 × 3 |
| Flattening layer | 10200 | — |
| Fully connected layer | 1024 | 1024 |
| Fully connected layer | 1024 | 1024 |
| Output layer | 2 | 2 |

Exemplarily, when the target MI-EEG signal corresponds to the second known action, in this embodiment, the first target MI features extracted by the initial feature extraction model for the target MI-EEG signal may further be inputted to the initial classification model, to obtain a third classification result outputted by the initial classification model. The third classification result is used for representing an action predicted to be performed in the target MI-EEG signal. The third classification result may be the action (corresponding to the known action having the highest probability) predicted to be performed in the target MI-EEG signal determined according to a probability of each known action predicted to be performed in the target MI-EEG signal determined by the first target MI features.

In step S206, in a case that the first known action corresponding to the source MI-EEG signal is inconsistent with the action predicted to be performed, represented by the first classification result, of the source MI-EEG signal, or a similarity between the feature distribution of the first source MI features and the feature distribution of the first target MI features is less than the first predetermined threshold, the model parameter of the initial feature extraction model and/or the model parameter of the initial classification model are/is adjusted to obtain the target feature extraction model and the target classification model.

That is, after the first source MI features, the first target MI features, and the first classification result are obtained, it may be determined whether the first known action corresponding to the source MI-EEG signal is consistent with the action predicted to be performed, represented by the first classification result, of the source MI-EEG signal, and whether a similarity between the feature distribution of the first source MI features and the feature distribution of the first target MI features is less than the first predetermined threshold. The first predetermined threshold may be a preset fixed value, or may be a value determined according to an objective function. When a first known action corresponding to the source MI-EEG signal is inconsistent with the action predicted to be performed, represented by the first classification result, of the source MI-EEG signal, or a similarity between a feature distribution of the first source MI features and a feature distribution of the first target MI features is less than a first predetermined threshold, it may be determined that the model does not converge, and the model parameter of the initial feature extraction model and/or the model parameter of the initial classification model need/needs to be adjusted, to obtain a target feature extraction model and a target classification model. A similarity between a feature distribution of second source MI features used for representing the source MI-EEG signal that are outputted by the target feature extraction model and a feature distribution of second target MI features used for representing the target MI-EEG signal that are outputted by the target feature extraction model is greater than or equal to the first predetermined threshold, and an action predicted to be performed, represented by a second classification result outputted by the target classification model, of the source MI-EEG signal is consistent with the first known action. The second classification result is the action (corresponding to the known action having the highest probability) predicted to be performed in the source MI-EEG signal determined by the target classification model according to a probability of each known action predicted to be performed in the source MI-EEG signal determined by the second source MI features.

Exemplarily, when the target MI-EEG signal corresponds to the second known action, and the third classification result used for representing the action predicted to be performed in the target MI-EEG signal has been determined by using the initial classification model, when step 206 is performed according to the method provided in the embodiments of this disclosure, the step of adjusting the model parameter of the initial feature extraction model and/or the model parameter of the initial classification model to obtain the target feature extraction model and the target classification model may be performed when it is determined that the first known action is inconsistent with the action predicted to be performed, represented by the first classification result, of the source MI-EEG signal, or that the second known action is inconsistent with the action predicted to be performed, represented by the third classification result, of the target MI-EEG signal, or that a similarity between the feature distribution of the first source MI features and the feature distribution of the first target MI features is less than the first predetermined threshold.

For example, the similarity between the feature distribution of the first source MI features and the feature distribution of the first target MI features may be determined by using a domain discrimination model or by using other metrics such as a cosine distance, a Manhattan distance, and a Chebyshev distance.

As an exemplary implementation, the adjusting a model parameter of the initial feature extraction model and/or a model parameter of the initial classification model to obtain a target feature extraction model and a target classification model includes: inputting the first source MI features and the first target MI features to an initial domain discrimination model, to obtain a first source discrimination result and a first target discrimination result, the initial domain discrimination model being used to: determine, according to the feature distribution of the first source MI features, a probability that the source MI-EEG signal belongs to the source domain and a probability that the source MI-EEG signal belongs to the target domain, and determine, according to the feature distribution of the first target MI features, a probability that the target MI-EEG signal belongs to the source domain and a probability that the target MI-EEG signal belongs to the target domain; and successively adjusting the model parameter of the initial MI recognition model (which includes the initial feature extraction model and the initial classification model) and a model parameter of the initial domain discrimination model by using the source MI-EEG signal and the target MI-EEG signal through training of a plurality of iterations, to obtain the target MI recognition model (which includes the target feature extraction model and the target classification model) and a target domain discrimination model, where the target domain discrimination model can determine, according to the second source MI features (features extracted from the source MI-EEG signal by the target feature extraction model), a probability that the source MI-EEG signal belongs to the source domain and a probability that the source MI-EEG signal belongs to the target domain, a difference between the two probabilities is less than or equal to a second predetermined threshold, and the second predetermined threshold may be a fixed threshold, or may be changed according to a target loss function.

During specific implementation, as shown in FIG. 7, preprocessed signals (including the source MI-EEG signal from the source domain and the target MI-EEG signal from the target domain) may be inputted to a feature extractor (the initial feature extraction model) designed to process EEG signals based on the CNN, a classifier (the initial classification model), and a domain discriminator (the initial domain discrimination model). During the training process, after the feature extractor and the classifier are updated, the domain discriminator is updated, so as to perform loop iterations. A final model classifier (the MI recognition model including the target feature extraction model and the target classification model) can accurately recognize the MI classification included in the inputted EEG signal. The domain discriminator may be a multi-layer fully connected structure based on the CNN, and the network structure may be shown in FIG. 2.

TABLE 2

| Layer name | Output size | Network |
|---|---|---|
| Input layer | 10200 | — |
| Fully connected layer | 1024 | 1024 |
| Fully connected layer | 512 | 512 |
| Fully connected layer | 1 | 1 |

Figure 6:
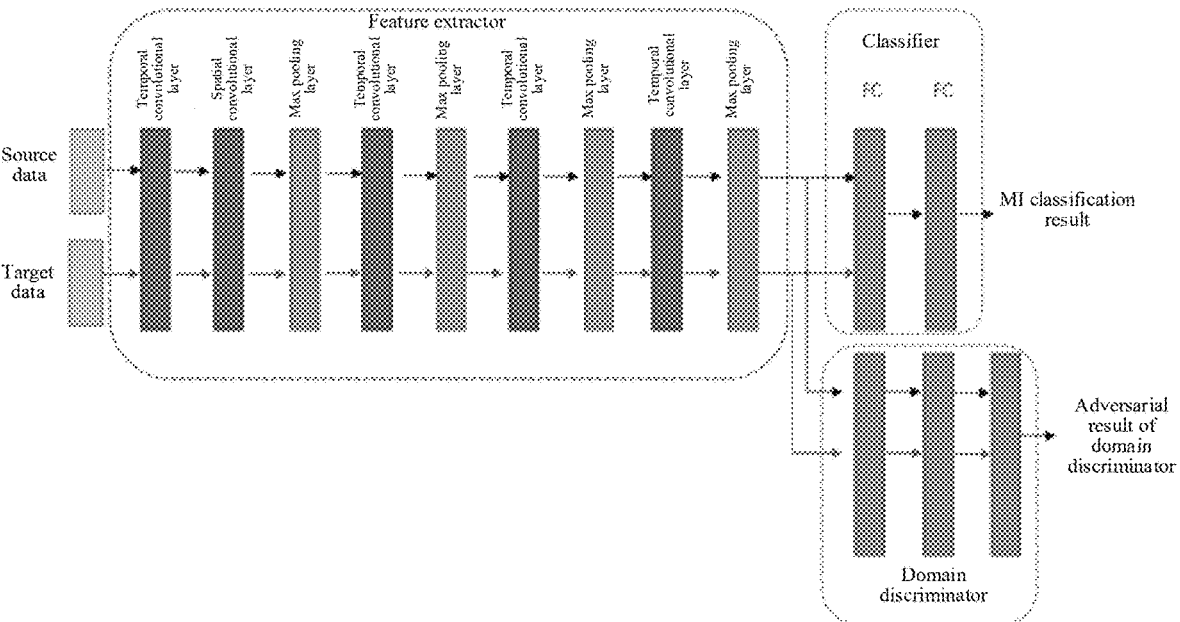
FIG. 6 is a schematic diagram of yet still another optional method for processing an MI-EEG signal according to an embodiment of this disclosure.

As shown in FIG. 6, a training model using the feature extractor, the classifier, and the domain discriminator may be a domain-adaptive MI deep decoding model based on discrimination adversary. MI-related features of subjects in the source domain are extracted through deep learning for classification and decoding. In addition, the domain-adaptive branch of the discrimination network adversary is combined to cause deep EEG signal features of target subjects and the features of the source domain to reach an indistinguishable balance.

In order to further optimize the discrimination network branch, the method of "metric learning" may be used, and an MMD loss function and an adversarial loss function are constrained, so as to further reduce distribution distances of the EEG signal features between the target subject and the subject in the source domain, thereby improving the decoding accuracy of the target subject.

Exemplarily, the loss function (objective function) used for loop iterations may include two parts, respectively: a feature extractor and classifier branch loss function and a $L_G$ domain discriminator branch loss function $L_D$. $L_G$ includes three parts of the loss function, which are respectively:

1) a loss function $L_{ce}$ used to determine the MI classification, which may be a cross-entropy loss function;

2) an adversarial loss function $L_{Gadv}$; and 3) a loss function $L_{mmd}$ used to determine the distribution similarity of the features generated by the feature extractor of the source domain and the target domain.

The formula of the loss functions may be shown in formula (1):

$$
\begin{cases}
L_G = L_{ce} + \alpha L_{Gadv} + \beta L_{mmd} & (1) \\
L_{ce} = -[y\log\hat{y} + (1-y)\log(1-\hat{y})] \\
L_{Gadv} = \log(1 - D(G(z))) \\
L_{mmd} = \dfrac{1}{c}\sum_{j=1}^{c} sup_f \left\| \dfrac{1}{m} f(x_i^j) - \dfrac{1}{n} f(z_i^j) \right\|^2
\end{cases}
$$

$\alpha$ and $\beta$ are weights between different loss functions, y is a real label, and is a prediction label. D and G respectively represent a domain discriminator network and a feature extractor network, x represents a sample of the source domain, z represents a sample of the target domain, and C represents a quantity of categories. f respectively represents feature layers of the feature extractor. $m_j$ represents a quantity of samples in a $j^{th}$ category of MI source domain, and $n_j$ represents a quantity of samples in the $j^{th}$ category of target domain.

The domain discriminator may select the minimum adversarial loss function, which may be shown in formula (2):

$$
L_{Dadv} = -\log D(G(x)) - \log(1 - D(G(z))) \tag{2}
$$

By using the transfer learning method of domain discriminant adversarial learning and using the EEG data of other subjects, the problem of overfitting easily caused by a small amount of subject independent training data and a large number of deep learning parameters may be resolved, and the accuracy of the model of the target subject is also improved. The method for processing an MI-EEG signal is described. The method for processing an MI-EEG signal provided in this example can alleviate the problem of a small amount of training data for EEG signals of a single subject, greatly improve the application range of a deep convolutional network on small sample EEG signals, and provide more possibilities for decoding EEG signals by deep models. The method for processing an MI-EEG signal in this example may be performed by a server, and may include a training phase and a test phase.

During the training, a source MI-EEG signal belonging to a source domain and a target MI-EEG signal belonging to a target domain are inputted to an initial feature extraction model, to obtain first source MI features and first target MI features; the first source MI features are inputted to an initial classification model, to obtain a first classification result outputted by the initial classification model, where the first classification result is used for representing a prediction of the initial classification model for an action performed by the source MI-EEG signal; and the source MI-EEG features and the target MI-EEG features are inputted to the domain discrimination model to obtain a distribution source prediction of the inputted MI-EEG features.

When the first known action corresponding to the source MI-EEG signal is inconsistent with the action performed by the source MI-EEG signal that is predicted by the initial classification model, or a similarity between the feature distribution of the first source MI features and the feature distribution of the first target MI features is less than the first predetermined threshold, the model loss function is minimized according to the inputted first source/target EEG signal, and the model parameter of the initial feature extraction model, and/or the model parameter of the initial classification model, and/or the model parameter of the domain discrimination model are/is adjusted to obtain the target feature extraction model and the target classification model.

During the test, the target MI-EEG signal is inputted to the target extraction model and the target classification model, so that the action performed by the target MI-EEG signal may be predicted. After the MI recognition model is obtained, the target subject test set may be used for verifying the accuracy and generalization capability of the MI recognition model obtained through training or for predicting MI intention of the target subject.

As shown in FIG. 8, during testing of the feature extractor (that is, the target extraction model) and the classifier (that is, the target classification model) by using MI-EEG signals in the test set, the MI-EEG signals in the test set may be preprocessed first. For the specific implementation process of preprocessing, reference may be made to the relevant description in FIG. 5.

The method for processing an MI-EEG signal through unsupervised learning may support unlabeled subject samples as the target domain, and train efficient and useful EEG decoding models, so as to make the application of BCIs more practical. According to another aspect of the embodiments of this disclosure, a method for processing an MI-EEG signal is provided. Exemplarily, the above method for processing an MI-EEG signal may be applied to, but is not limited to, the network architecture shown in FIG. 1.

Exemplarily, in this embodiment, as an exemplary implementation, as shown in FIG. 9, the method for processing an MI-EEG signal may include the following steps.

S902: Acquire a to-be-recognized MI-EEG signal, where the to-be-recognized MI-EEG signal is an MI-EEG signal collected from a target object.

S904: Input the to-be-recognized MI-EEG signal to a target feature extraction model, to obtain to-be-recognized MI features used for representing the to-be-recognized MI-EGG signal, and input the to-be-recognized MI features to a target classification model, to obtain a target classification result outputted by the target classification model, where a similarity between feature distributions of different MI features extracted by the target feature extraction model for different MI training signals is greater than or equal to a first similarity threshold, the different MI training signals include a target MI-EEG signal and a source MI-EEG signal corresponding to a first known action, an action predicted to be performed in the source MI-EEG signal that is represented by a classification result outputted by the target classification model is consistent with the first known action, the classification result is a classification result determined by the target classification model according to source MI features extracted from the source MI-EEG signal by the target feature extraction model, and the target classification result is used for representing an action predicted to be performed in the to-be-recognized MI-EEG signal.

S906: Control, according to the target classification result, a target device matching the target object to perform the action predicted to be performed in the to-be-recognized MI-EEG signal.

Exemplarily, the method for processing an MI-EEG signal may be applied to, but is not limited to, the process of transmission and control of ideas. For example, a BCI system combined with an exoskeleton robot may be used for active rehabilitation of motor functions of patients with hemiplegia or cerebral stroke, a BCI system combined with an electric wheelchair can help users with physical disabilities to travel freely, and a brain-computer-game system combined with a game can achieve activities of objects (including, but not limited to, at least one of the following: characters, articles, and the like) in a virtual world controlled by a human body through ideas and imagination.

In this way, action types of the to-be-recognized MI-EEG signals are recognized by using the target feature extraction model and the target classification model. However, feature distributions of different MI-EEG signals extracted by the target feature extraction model are similar, and the target classification model may correctly recognize the first known action corresponding to the source MI-EEG signal according to the source MI feature, which resolves the technical problem, improving the generalization capability of the MI recognition model (including the obtained feature extraction model and classification model) and the accuracy of decoding.

Furthermore, end-to-end decoding and classification is performed for MI-EEG signals through deep learning, and the decoding result may be obtained directly by inputting the original signal without too much prior knowledge of manual extraction of features, so that the model is more universal.

For ease of description, the foregoing method embodiments are stated as a series of action combinations. However, a person skilled in the art is to learn that this disclosure is not limited to the described sequence of the actions, because according to this disclosure, some steps may use another sequence or may be simultaneously performed. In addition, a person skilled in the art is also to learn that the embodiments described in this specification are all exemplary embodiments, and the involved actions and modules are not necessarily required to this disclosure.

Figure 10:
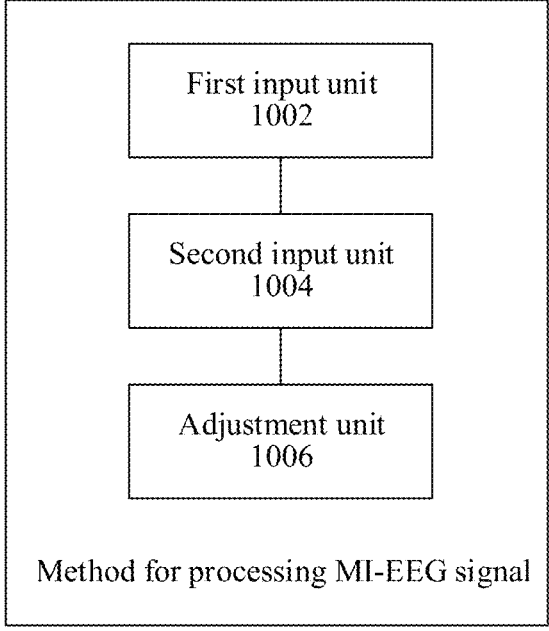
FIG. 10 is a schematic structural diagram of an optional apparatus for processing an MI-EEG signal according to an embodiment of this disclosure.

According to still another aspect of the embodiments of this disclosure, an apparatus for processing an MI-EEG signal used for implementing the above method for processing an MI-EEG signal is further provided. As shown in FIG. 10, the apparatus includes:

(1) a first input unit 1002, configured to input a source MI-EEG signal belonging to a source domain and a target MI-EEG signal belonging to a target domain to an initial feature extraction model, to obtain first source MI features used for representing the source MI-EEG signal and first target MI features used for representing the target MI-EEG signal;

(2) a second input unit 1004, configured to input the first source MI features to an initial classification model, to obtain a first classification result outputted by the initial classification model, the first classification result being used for representing an action predicted to be performed in the source MI-EEG signal; and (3) an adjustment unit 1006, configured to adjust a model parameter of the initial feature extraction model and/or a model parameter of the initial classification model when a first known action corresponding to the source MI-EEG signal is inconsistent with the action predicted to be performed, represented by the first classification result, of the source MI-EEG signal, or a similarity between a feature distribution of the first source MI features and a feature distribution of the first target MI features is less than a first predetermined threshold, to obtain a target feature extraction model and a target classification model, a similarity between a feature distribution of second source MI features used for representing the source MI-EEG signal that are outputted by the target feature extraction model and a feature distribution of second target MI features used for representing the target MI-EEG signal that are outputted by the target feature extraction model being greater than or equal to the first predetermined threshold, and an action predicted to be performed in the source MI-EEG signal that is represented by a second classification result outputted by the target classification model being consistent with the first known action.

Exemplarily, the apparatus for processing an MI-EEG signal may be applied to, but is not limited to, the process of transmission and control of ideas. For example, a BCI system combined with an exoskeleton robot may be used for active rehabilitation of motor functions of patients with hemiplegia or cerebral stroke, a BCI system combined with an electric wheelchair can help users with physical disabilities to travel freely, and a brain-computer-game system combined with a game can achieve activities of objects (including, but not limited to, at least one of the following: characters, articles, and the like) in a virtual world controlled by a human body through ideas and imagination.

Exemplarily, the first input unit 1002 may be configured to perform the foregoing step S202, the second input unit 1004 may be configured to perform the foregoing step S204, and the adjustment unit 1006 may be configured to perform the foregoing step S206.

In this way, the feature extraction model and the classification model are trained by using the source MI-EEG signal corresponding to the first known action and the target MI-EEG signal, so that the features of the source MI-EEG signal and the features of the target MI-EEG signal that are extracted by the feature extraction model are distributed in a similar manner, and the classification model can correctly recognize the first known action, which resolves the technical problem of low accuracy of decoding MI-EEG signals of different objects by an MI recognition model due to the MI-EEG signals varying greatly among subject individuals in the related art, and improves the generalization capability of the MI recognition model and the accuracy of decoding.

As an exemplary implementation, the adjustment unit 1006 includes:

(1) a first input module, configured to input the first source MI features and the first target MI features to an initial domain discrimination model, to obtain a first source discrimination result and a first target discrimination result, the initial domain discrimination model being used to: determine, according to the feature distribution of the first source MI features, a probability that the source MI-EEG signal belongs to the source domain and a probability that the source MI-EEG signal belongs to the target domain, and determine, according to the feature distribution of the first target MI features, a probability that the target MI-EEG signal belongs to the source domain and a probability that the target MI-EEG signal belongs to the target domain; and (2) an adjustment module, configured to adjust the model parameter of the initial feature extraction model and/or the model parameter of the initial classification model, and a model parameter of the initial domain discrimination model by using the source MI-EEG signal and the target MI-EEG signal by means of a plurality of iterations, to obtain a target feature extraction model, a target classification model, and a target domain discrimination model, a difference between the probability that the source MI-EEG signal belongs to the source domain and the probability that the source MI-EEG signal belongs to the target domain that are determined by the target domain discrimination model according to the second source MI features being less than or equal to a second predetermined threshold, and a difference between the probability that the target MI-EEG signal belongs to the source domain and the probability that the target MI-EEG signal belongs to the target domain that are determined by the target domain discrimination model according to the second target MI features being less than or equal to the second predetermined threshold.

As an exemplary implementation, the above apparatus further includes:

(1) a third input unit, configured to: when the target MI-EEG signal corresponds to a second known action, before the adjusting a model parameter of the initial feature extraction model and/or a model parameter of the initial classification model to obtain a target feature extraction model and a target classification model, input the first target MI features to the initial classification model to obtain a third classification result outputted by the initial classification model, the third classification result being used for representing an action predicted to be performed in the target MI-EEG signal; and (2) a determination unit, configured to trigger, when it is determined that the first known action is inconsistent with the action predicted to be performed in the source MI-EEG signal, or that the second known action is inconsistent with the action predicted to be performed, represented by the third classification result, of the target MI-EEG signal, or that a similarity between the feature distribution of the first source MI features and the feature distribution of the first target MI features is less than the first predetermined threshold, the adjustment unit 1006 to perform the step of adjusting the model parameter of the initial feature extraction model and/or the model parameter of the initial classification model, to obtain the target feature extraction model and the target classification model.

As an exemplary implementation, the above apparatus further includes:

(1) a first acquisition unit, configured to acquire an initial source MI-EEG signal belonging to the source domain and an initial target MI-EEG signal belonging to the target domain before the inputting a source MI-EEG signal belonging to the source domain and a target MI-EEG signal belonging to the target domain to an initial feature extraction model;

(2) a first preprocessing unit, configured to preprocess the initial source MI-EEG signal to obtain the source MI-EEG signal; and (3) a second preprocessing unit, configured to preprocess the initial target MI-EEG signal to obtain the target MI-EEG signal.

In this way, the initial source MI-EEG signal and the initial target MI-EEG signal are preprocessed, so that the MI-EEG signal can be optimized, and the effectiveness of training the MI-EEG signal recognition model can be improved.

As an exemplary implementation, the first preprocessing unit includes:

(1) a first intercepting module, configured to intercept a signal of a predetermined duration from the initial source MI-EEG signal, to obtain a first source MI-EEG signal;

(2) a first filtration module, configured to input the first source MI-EEG signal to a band-pass filter, to obtain a second source MI-EEG signal, the band-pass filter being configured to filter out, from the first source MI-EEG signal, a signal not in a frequency band range of the band-pass filter; and (3) a first standardization module, configured to standardize the second source MI-EEG signal to obtain the source MI-EEG signal.

As an exemplary implementation, the second preprocessing unit includes:

(1) a second intercepting module, configured to intercept a signal of a predetermined duration from the initial target MI-EEG signal, to obtain a first target MI-EEG signal;

(2) a second filtration module, configured to input the first target MI-EEG signal to a band-pass filter, to obtain a second target MI-EEG signal, the band-pass filter being configured to filter out, from the first target MI-EEG signal, a signal not in a band-pass frequency band range; and (3) a second standardization module, configured to standardize the second target MI-EEG signal to obtain the target MI-EEG signal.

In this way, the initial MI-EEG signal is preprocessed to filter out noise data, and lengths of the MI-EEG signals are unified and the MI-EEG signals are standardized, so as to improve the effectiveness of training the MI-EEG signal recognition model.

As an exemplary implementation, the above apparatus further includes:

(1) a transmission unit, configured to transmit a target instruction to a collection device before the source MI-EEG signal belonging to the source domain and the target MI-EEG signal belonging to the target domain are inputted to the initial feature extraction model, where the target instruction is used for indicating a to-be-performed first known action; and (2) a receiving unit, configured to receive the source MI-EEG signal transmitted from the collection device, where the source MI-EEG signal is an MI-EEG signal collected by the collection device within a particular time period after receiving the target instruction.

In this way, the collection device is instructed to collect MI-EEG signals by using the target instruction used for indicating the to-be-performed first known action, so that the source MI-EEG signal corresponding to the first known action may be obtained, so as to guarantee the accuracy of acquiring the source MI-EEG signal.

Figure 11:
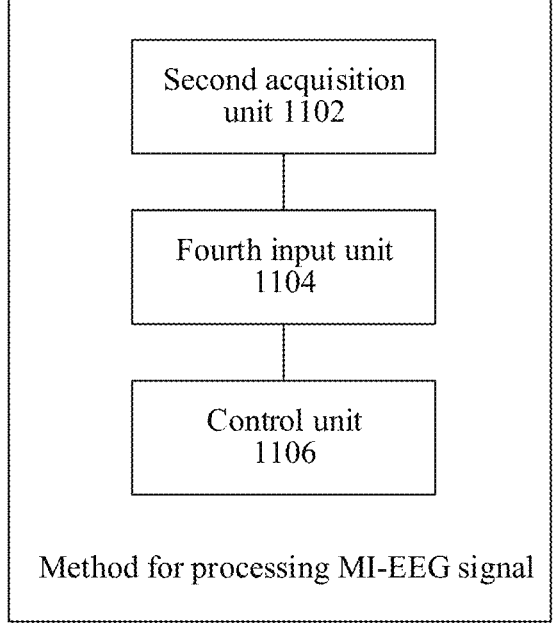
FIG. 11 is a schematic structural diagram of another optional apparatus for processing an MI-EEG signal according to an embodiment of this disclosure.

According to still another aspect of the embodiments of this disclosure, an apparatus for processing an MI-EEG signal used for implementing the above method for processing an MI-EEG signal is further provided. As shown in FIG. 11, the apparatus includes:

(1) a second acquisition unit 1102, configured to acquire a to-be-recognized MI-EEG signal, the to-be-recognized MI-EEG signal being an MI-EEG signal collected from a target object;

(2) a fourth input unit 1104, configured to successively input the to-be-recognized MI-EEG signal to a target feature extraction model, to obtain to-be-recognized MI features used for representing the to-be-recognized MI-EGG signal, and input the to-be-recognized MI features to a target classification model, to obtain a target classification result outputted by the target classification model, a similarity between feature distributions of different MI features extracted by the target feature extraction model for different MI training signals being greater than or equal to a first similarity threshold, the different MI training signals including a target MI-EEG signal and a source MI-EEG signal corresponding to a first known action, an action predicted to be performed in the source MI-EEG signal that is represented by a classification result outputted by the target classification model being consistent with the first known action, the classification result being a classification result determined by the target classification model according to source MI features extracted from the source MI-EEG signal by the target feature extraction model, and the target classification result being used for representing an action predicted to be performed in the to-be-recognized MI-EEG signal; and (3) a control unit 1106, configured to control, according to the target classification result, a target device matching the target object to perform the action predicted to be performed in the to-be-recognized MI-EEG signal.

Exemplarily, the apparatus for processing an MI-EEG signal may be applied to, but is not limited to, the process of transmission and control of ideas. For example, a BCI system combined with an exoskeleton robot may be used for active rehabilitation of motor functions of patients with hemiplegia or cerebral stroke, a BCI system combined with an electric wheelchair can help users with physical disabilities to travel freely, and a brain-computer-game system combined with a game can achieve activities of objects (including, but not limited to, at least one of the following: characters, articles, and the like) in a virtual world controlled by a human body through ideas and imagination.

Exemplarily, the second acquisition unit 1102 may be configured to perform the foregoing step S902, the fourth input unit 1104 may be configured to perform the foregoing step S904, and the control unit 1106 may be configured to perform the foregoing step S906.

In this way, action types of the to-be-recognized MI-EEG signals are recognized by using the target feature extraction model and the target classification model. However, feature distributions of different MI-EEG signals extracted by the target feature extraction model are similar, and the target classification model may correctly recognize the first known action according to the target MI feature, which resolves the technical problem of low accuracy of decoding MI-EEG signals of different objects by an MI recognition model due to the MI-EEG signals varying greatly among subject individuals in the related art, and improves the generalization capability of the MI recognition model (including the obtained feature extraction model and classification model) and the accuracy of decoding.

The term module (and other similar terms such as unit, submodule, subunit, etc.) in this disclosure may refer to a software module, a hardware module, or a combination thereof. A software module (e.g., computer program) may be developed using a computer programming language. A hardware module may be implemented using processing circuitry and/or memory. Each module can be implemented using one or more processors (or processors and memory). Likewise, a processor (or processors and memory) can be used to implement one or more modules. Moreover, each module can be part of an overall module that includes the functionalities of the module.

Each of the above modules may be implemented by software or hardware. For the means of hardware, implementation may be performed by using the following method, which is not limited thereto: the above modules are all located in the same processor, or the above modules are located in different processors in the form of any combination.

According to still another aspect of the embodiments of this disclosure, a storage medium is further provided, storing a computer program, where the computer program is configured to, when run, perform the step in any one of the foregoing method embodiments.

Exemplarily, in this embodiment, the storage medium may be set to store a computer program for performing the following steps:

S1: Input a source MI-EEG signal belonging to a source domain and a target MI-EEG signal belonging to a target domain to an initial feature extraction model, to obtain first source MI features used for representing the source MI-EEG signal and first target MI features used for representing the target MI-EEG signal.

S2: Input the first source MI features to an initial classification model, to obtain a first classification result outputted by the initial classification model, the first classification result being used for representing an action predicted to be performed in the source MI-EEG signal.

S3: Adjust a model parameter of the initial feature extraction model and/or a model parameter of the initial classification model when a first known action corresponding to the source MI-EEG signal is inconsistent with the action predicted to be performed, represented by the first classification result, of the source MI-EEG signal, or a similarity between a feature distribution of the first source MI features and a feature distribution of the first target MI features is less than a first predetermined threshold, to obtain a target feature extraction model and a target classification model, a similarity between a feature distribution of second source MI features used for representing the source MI-EEG signal that are outputted by the target feature extraction model and a feature distribution of second target MI features used for representing the target MI-EEG signal that are outputted by the target feature extraction model being greater than or equal to the first predetermined threshold, and an action predicted to be performed in the source MI-EEG signal that is represented by a second classification result outputted by the target classification model being consistent with the first known action.

Alternatively, the following steps are performed.

S1': Acquire a to-be-recognized MI-EEG signal, where the to-be-recognized MI-EEG signal is an MI-EEG signal collected from a target object.

S2': Input the to-be-recognized MI-EEG signal to a target feature extraction model, to obtain to-be-recognized MI features used for representing the to-be-recognized MI-EGG signal, and input the to-be-recognized MI features to a target classification model, to obtain a target classification result outputted by the target classification model, where a similarity between feature distributions of different MI features extracted by the target feature extraction model for different MI training signals is greater than or equal to a first similarity threshold, the different MI training signals include a target MI-EEG signal and a source MI-EEG signal corresponding to a first known action, an action predicted to be performed in the source MI-EEG signal that is represented by a classification result outputted by the target classification model is consistent with the first known action, the classification result is a classification result determined by the target classification model according to source MI features extracted from the source MI-EEG signal by the target feature extraction model, and the target classification result is used for representing an action predicted to be performed in the to-be-recognized MI-EEG signal.

S3': Control, according to the target classification result, a target device matching the target object to perform the action predicted to be performed in the to-be-recognized MI-EEG signal.

Exemplarily, in this embodiment, the storage medium may be set to store a computer program for performing the following steps:

Exemplarily, in this embodiment, a person of ordinary skill in the art may understand that all or some of the steps of the methods in the foregoing embodiments may be implemented by a program indicating relevant hardware of the terminal device. The program may be stored in a computer-readable storage medium. The storage medium may include a flash disk, a read-only memory (ROM), a random access memory (RAM), a magnetic disk, an optical disc, and the like.

Figure 12:
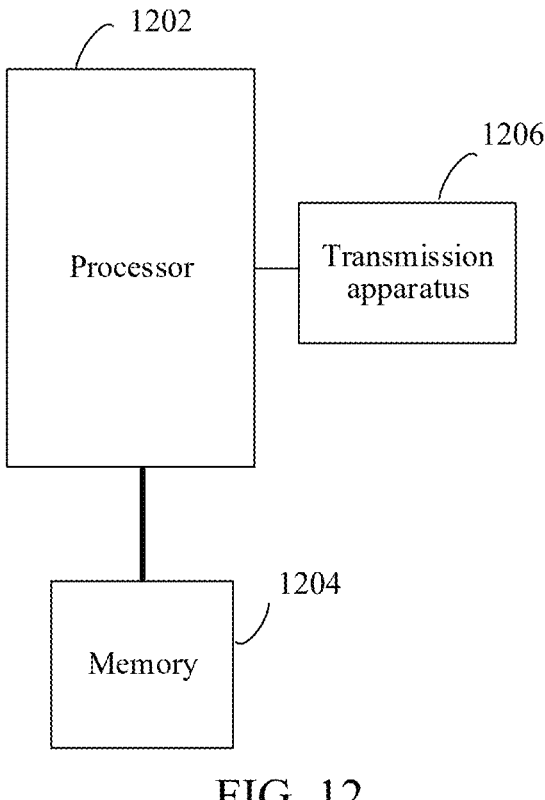
FIG. 12 is a schematic structural diagram of an optional electronic device according to an embodiment of this disclosure.

According to still another aspect of the embodiments of this disclosure, an electronic device configured to perform the method for processing an MI-EEG signal is further provided. As shown in FIG. 12, the electronic device may include: a processor 1202, a memory 1204, a transmission apparatus 1206, and the like. The memory stores a computer program, and the processor is configured to perform steps in any one of the method embodiments through the computer program.

Exemplarily, in this embodiment, the electronic device may be located in at least one of a plurality of network devices in a computer network.

Exemplarily, in this embodiment, the processor may be configured to perform the following steps through a computer program:

S1: Input a source MI-EEG signal belonging to a source domain and a target MI-EEG signal belonging to a target domain to an initial feature extraction model, to obtain first source MI features used for representing the source MI-EEG signal and first target MI features used for representing the target MI-EEG signal.

S2: Input the first source MI features to an initial classification model, to obtain a first classification result outputted by the initial classification model, the first classification result being used for representing an action predicted to be performed in the source MI-EEG signal.

S3: Adjust a model parameter of the initial feature extraction model and/or a model parameter of the initial classification model when a first known action corresponding to the source MI-EEG signal is inconsistent with the action predicted to be performed, represented by the first classification result, of the source MI-EEG signal, or a similarity between a feature distribution of the first source MI features and a feature distribution of the first target MI features is less than a first predetermined threshold, to obtain a target feature extraction model and a target classification model, a similarity between a feature distribution of second source MI features used for representing the source MI-EEG signal that are outputted by the target feature extraction model and a feature distribution of second target MI features used for representing the target MI-EEG signal that are outputted by the target feature extraction model being greater than or equal to the first predetermined threshold, and an action predicted to be performed in the source MI-EEG signal that is represented by a second classification result outputted by the target classification model being consistent with the first known action.

Alternatively, the following steps are performed.

S1': Acquire a to-be-recognized MI-EEG signal, where the to-be-recognized MI-EEG signal is an MI-EEG signal collected from a target object.

S2': Input the to-be-recognized MI-EEG signal to a target feature extraction model, to obtain to-be-recognized MI features used for representing the to-be-recognized MI-EGG signal, and input the to-be-recognized MI features to a target classification model, to obtain a target classification result outputted by the target classification model, where a similarity between feature distributions of different MI features extracted by the target feature extraction model for different MI training signals is greater than or equal to a first similarity threshold, the different MI training signals include a target MI-EEG signal and a source MI-EEG signal corresponding to a first known action, an action predicted to be performed in the source MI-EEG signal that is represented by a classification result outputted by the target classification model is consistent with the first known action, the classification result is a classification result determined by the target classification model according to source MI features extracted from the source MI-EEG signal by the target feature extraction model, and the target classification result is used for representing an action predicted to be performed in the to-be-recognized MI-EEG signal.

S3': Control, according to the target classification result, a target device matching the target object to perform the action predicted to be performed in the to-be-recognized MI-EEG signal.

Exemplarily, in this embodiment, the processor may be configured to perform the following steps through a computer program:

Exemplarily, a person of ordinary skill in the art may understand that the structure shown in FIG. 12 is only an example. The electronic device may alternatively be a server, an MI-EEG signal collection device, or the like. FIG. 12 does not constitute a limitation on the structure of the electronic device. For example, the electronic device may further include more or fewer components (such as a network interface) than those shown in FIG. 12, or have a configuration different from that shown in FIG. 12.

The memory 1204 may be configured to store a software program and module, for example, a program instruction/module corresponding to the method and apparatus for processing an MI-EEG signal in the embodiments of this disclosure. The processor 1202 runs the software program and module stored in the memory 1204, to implement various functional applications and data processing, that is, implement the foregoing method for processing an MI-EEG signal. The memory 1204 may include a high-speed random memory, and may also include a non-volatile memory, for example, one or more magnetic storage apparatuses, a flash memory, or another non-volatile solid-state memory. In some examples, the memory 1204 may further include memories remotely disposed relative to the processor 1202, and the remote memories may be connected to a terminal through a network. The foregoing examples of the network include, but are not limited to, the Internet, an intranet, a local area network, a mobile communication network, and a combination thereof.

A transmission device 1206 is configured to receive or transmit data through a network. Specific examples of the foregoing network may include a wired network and a wireless network. In an example, the transmission apparatus 1206 includes a network interface controller (NIC). The NIC may be connected to another network device and a router by using a network cable, to communicate with the Internet or a local area network. In an example, the transmission apparatus 1206 is a radio frequency (RF) module, which communicates with the Internet in a wireless manner.

The sequence numbers of the foregoing embodiments of this disclosure are merely for description purpose, and are not intended to indicate the preference among the embodiments.

If the integrated unit in the foregoing embodiments is implemented in the form of a software function unit and sold or used as an independent product, the integrated unit may be stored in the foregoing computer-readable storage medium. Based on such an understanding, the technical solutions of this disclosure essentially, or a part contributing to the related art, or all or a part of the technical solution may be implemented in a form of a software product. The computer software product is stored in a storage medium and includes several instructions for instructing one or more computer devices (which may be a PC, a server, a network device, or the like) to perform all or some of the steps of the methods in the embodiments of this disclosure.

In the foregoing embodiments of this disclosure, descriptions of the embodiments have different emphases. As for parts that are not described in detail in one embodiment, reference may be made to the relevant descriptions of the other embodiments.

In the several embodiments provided in this disclosure, it is to be understood that the disclosed client may be implemented in other manners. The described apparatus embodiments are merely exemplary. For example, the unit division is merely logical function division, and may use other division manners during actual implementation. For example, a plurality of units or components may be combined or integrated into another system, or some features may be omitted or not performed. In addition, the coupling, or direct coupling, or communication connection between the displayed or discussed components may be the indirect coupling or communication connection by using some interfaces, units, or modules, and may be electrical or of other forms.

The units described as separate parts can or cannot be physically separate. Parts displayed as units can or cannot be physical units, and can be located in one position, or can be distributed on a plurality of network units. Some or all of the units may be selected according to actual needs to achieve the objectives of the solutions of the embodiments.

In addition, functional units in the embodiments of this disclosure may be integrated into one processing unit, or each of the units may exist alone physically, or two or more units may be integrated into one unit. The integrated unit may be implemented in a form of hardware, or may be implemented in a form of a software functional unit.

The foregoing descriptions are merely exemplary implementations of this disclosure. A person of ordinary skill in the art may make some improvements and polishing without departing from the principle of this disclosure and the improvements and polishing shall fall within the protection scope of this disclosure.

What is claimed is:

1. A method for processing a motor imagery (MI) electroencephalogram (EEG) signal, performed by an electronic device, the method comprising:

inputting a source MI-EEG signal belonging to a source domain and a target MI-EEG signal belonging to a target domain to an initial feature extraction model to obtain first source MI features representing the source MI-EEG signal and first target MI features representing the target MI-EEG signal;

inputting the first source MI features to an initial classification model to obtain a first classification result outputted by the initial classification model, the first classification result representing an action predicted to be performed in the source MI-EEG signal;

adjusting, in response to a first known action corresponding to the source MI-EEG signal is inconsistent with the action predicted to be performed of the source MI-EEG signal, or a similarity between a feature distribution of the first source MI features and a feature distribution of the first target MI features is less than a first predetermined threshold, a model parameter of the initial feature extraction model and/or a model parameter of the initial classification model to obtain a target feature extraction model and a target classification model, wherein the adjusting is performed iteratively using the source MI-EEG signal and the target MI-EEG signal, and a similarity between a feature distribution of second source MI features representing the source MI-EEG signal and outputted by the target feature extraction model and a feature distribution of second target MI features representing the target MI-EEG signal and outputted by the target feature extraction model is greater than or equal to the first predetermined threshold, and an action predicted to be performed, represented by a second classification result outputted by the target classification model, of the source MI-EEG signal that is consistent with the first known action; and controlling, according to the second classification result, a target device to perform the action predicted to be performed.

2. The method according to claim 1, wherein adjusting the model parameter of the initial feature extraction model and/or the model parameter of the initial classification model to obtain the target feature extraction model and the target classification model comprises:

inputting the first source MI features and the first target MI features to an initial domain discrimination model to obtain a first source discrimination result and a first target discrimination result, the initial domain discrimination model being used to:

determine, according to the feature distribution of the first source MI features, a probability that the source MI-EEG signal belongs to the source domain and a probability that the source MI-EEG signal belongs to the target domain, and determine, according to the feature distribution of the first target MI features, a probability that the target MI-EEG signal belongs to the source domain and a probability that the target MI-EEG signal belongs to the target domain; and adjusting the model parameter of the initial feature extraction model and/or the model parameter of the initial classification model and a model parameter of the initial domain discrimination model by using the source MI-EEG signal and the target MI-EEG signal via a plurality of iterations to obtain:

the target feature extraction model,
the target classification model, and
a target domain discrimination model, wherein a difference between the probability that the source MI-EEG signal belongs to the source domain and the probability that the source MI-EEG signal belongs to the target domain that are determined by the target domain discrimination model according to the second source MI features being less than or equal to a second predetermined threshold, and a difference between the probability that the target MI-EEG signal belongs to the source domain and the probability that the target MI-EEG signal belongs to the target domain that are determined by the target domain discrimination model according to the second target MI features being less than or equal to the second predetermined threshold.

3. The method according to claim 1, wherein when the target MI-EEG signal corresponds to a second known action, the method further comprises:

inputting the first target MI features to the initial classification model to obtain a third classification result outputted by the initial classification model, the third classification result representing an action predicted to be performed in the target MI-EEG signal; and performing the step of adjusting the model parameter of the initial feature extraction model and/or the model parameter of the initial classification model when it is determined that the first known action is inconsistent with the action expected to be performed in the source MI-EEG signal, or that the second known action is inconsistent with the action predicted to be performed, represented by the third classification result, of the target MI-EEG signal, or that a similarity between the feature distribution of the first source MI features and the feature distribution of the first target MI features is less than the first predetermined threshold.

4. The method according to claim 1, wherein before inputting the source MI-EEG signal belonging to the source domain and the target MI-EEG signal belonging to the target domain to the initial feature extraction model, the method further comprises:

acquiring an initial source MI-EEG signal belonging to the source domain and an initial target MI-EEG signal belonging to the target domain;

preprocessing the initial source MI-EEG signal to obtain the source MI-EEG signal; and preprocessing the initial target MI-EEG signal to obtain the target MI-EEG signal.

5. The method according to claim 4, wherein preprocessing the initial source MI-EEG signal to obtain the source MI-EEG signal comprises:

intercepting a signal of a predetermined duration from the initial source MI-EEG signal to obtain a first source MI-EEG signal;

inputting the first source MI-EEG signal to a band-pass filter, to obtain a second source MI-EEG signal; and standardizing the second source MI-EEG signal to obtain the source MI-EEG signal.

6. The method according to claim 4, wherein preprocessing the initial target MI-EEG signal to obtain the target MI-EEG signal comprises:

intercepting a signal of a predetermined duration from the initial target MI-EEG signal to obtain a first target MI-EEG signal;

inputting the first target MI-EEG signal to a band-pass filter, to obtain a second target MI-EEG signal; and standardizing the second target MI-EEG signal to obtain
the target MI-EEG signal.

7. The method according to claim 1, wherein before
inputting the source MI-EEG signal belonging to the source
domain and the target MI-EEG signal belonging to the target
domain to the initial feature extraction model, the method
further comprises:

transmitting a target instruction to a collection device, the
target instruction being used for indicating the first
known action to be performed; and receiving the source MI-EEG signal transmitted from the
collection device, the source MI-EEG signal being an
MI-EEG signal collected by the collection device
within a particular time period after receiving the target
instruction.

8. A method for processing a motor imagery (MI) elec-
troencephalogram (EEG) signal, performed by an electronic
device, the method comprising:

acquiring a to-be-recognized MI-EEG signal, the to-be-
recognized MI-EEG signal being an MI-EEG signal
collected from a target object;

inputting the to-be-recognized MI-EEG signal to a target
feature extraction model to obtain to-be-recognized MI
features representing the to-be-recognized MI-EEG
signal, and inputting the to-be-recognized MI features to a target
classification model to obtain a target classification
result outputted by the target classification model, wherein a similarity between feature distributions of
different MI features extracted by the target feature
extraction model for different MI training signals is
greater than or equal to a first similarity threshold, the
different MI training signals comprising a target MI-
EEG signal and a source MI-EEG signal corresponding
to a first known action, an action predicted to be performed in the source MI-EEG
signal that is represented by a classification result
outputted by the target classification model being con-
sistent with the first known action, the classification
result being a classification result determined by the
target classification model according to source MI
features extracted from the source MI-EEG signal by
the target feature extraction model, and the target
classification result being used for representing an
action predicted to be performed in the to-be-recog-
nized MI-EEG signal; and controlling, according to the target classification result, a
target device matching the target object to perform the
action predicted to be performed in the to-be-recog-
nized MI-EEG signal.

9. An electronic device, comprising a memory and a
processor, the memory storing a computer program, and the
processor being configured to execute the computer program
to cause the electronic device to perform the method of
claim 8.

10. An electronic device, comprising a memory and a
processor, the memory storing a computer program, and the
processor being configured to execute the computer program
to cause the electronic device to perform steps, comprising:

inputting a source MI-EEG signal belonging to a source
domain and a target MI-EEG signal belonging to a
target domain to an initial feature extraction model to
obtain first source MI features representing the source
MI-EEG signal and first target MI features representing
the target MI-EEG signal;

inputting the first source MI features to an initial classi-
fication model to obtain a first classification result outputted by the initial classification model, the first
classification result representing an action predicted to
be performed in the source MI-EEG signal;

adjusting, in response to a first known action correspond-
ing to the source MI-EEG signal is inconsistent with
the action predicted to be performed of the source
MI-EEG signal, or a similarity between a feature dis-
tribution of the first source MI features and a feature
distribution of the first target MI features is less than a
first predetermined threshold, a model parameter of the
initial feature extraction model and/or a model param-
eter of the initial classification model to obtain a target
feature extraction model and a target classification
model, wherein the adjusting is performed iteratively using the
source MI-EEG signal and the target MI-EEG signal,
and a similarity between a feature distribution of sec-
ond source MI features representing the source MI-
EEG signal and outputted by the target feature extrac-
tion model and a feature distribution of second target
MI features representing the target MI-EEG signal and
outputted by the target feature extraction model is
greater than or equal to the first predetermined thresh-
old, and an action predicted to be performed, repre-
sented by a second classification result outputted by the
target classification model, of the source MI-EEG sig-
nal that is consistent with the first known action; and control, according to the second classification result, a
target device to perform the action predicted to be
performed.

11. The electronic device of claim 10, wherein the pro-
cessor is configured to cause the electronic device to adjust
the model parameter of the initial feature extraction model
and/or the model parameter of the initial classification model
to obtain the target feature extraction model and the target
classification model by:

inputting the first source MI features and the first target
MI features to an initial domain discrimination model
to obtain a first source discrimination result and a first
target discrimination result, the initial domain discrimi-
nation model being used to:

determine, according to the feature distribution of the
first source MI features, a probability that the source
MI-EEG signal belongs to the source domain and a
probability that the source MI-EEG signal belongs to
the target domain, and determine, according to the feature distribution of the
first target MI features, a probability that the target
MI-EEG signal belongs to the source domain and a
probability that the target MI-EEG signal belongs to
the target domain; and adjusting the model parameter of the initial feature
extraction model and/or the model parameter of the
initial classification model and a model parameter of
the initial domain discrimination model by using the
source MI-EEG signal and the target MI-EEG signal
via a plurality of iterations to obtain:

the target feature extraction model,
the target classification model, and
a target domain discrimination model, wherein a difference between the probability that the
source MI-EEG signal belongs to the source domain
and the probability that the source MI-EEG signal
belongs to the target domain that are determined by the
target domain discrimination model according to the
second source MI features being less than or equal to a
second predetermined threshold, and a difference between the probability that the target MI-EEG signal belongs to the source domain and the probability that the target MI-EEG signal belongs to the target domain that are determined by the target domain discrimination model according to the second target MI features being less than or equal to the second predetermined threshold.

12. The electronic device of claim 10, wherein when the target MI-EEG signal corresponds to a second known action, the processor is configured to further cause the electronic device to perform steps, comprising:

inputting the first target MI features to the initial classification model to obtain a third classification result outputted by the initial classification model, the third classification result representing an action predicted to be performed in the target MI-EEG signal; and performing the step of adjusting the model parameter of the initial feature extraction model and/or the model parameter of the initial classification model when it is determined that the first known action is inconsistent with the action expected to be performed in the source MI-EEG signal, or that the second known action is inconsistent with the action predicted to be performed, represented by the third classification result, of the target MI-EEG signal, or that a similarity between the feature distribution of the first source MI features and the feature distribution of the first target MI features is less than the first predetermined threshold.

13. The electronic device of claim 10, wherein before inputting the source MI-EEG signal belonging to the source domain and the target MI-EEG signal belonging to the target domain to the initial feature extraction model, the processor is configured to further cause the electronic device to perform steps, comprising:

acquiring an initial source MI-EEG signal belonging to the source domain and an initial target MI-EEG signal belonging to the target domain;

preprocessing the initial source MI-EEG signal to obtain the source MI-EEG signal; and preprocessing the initial target MI-EEG signal to obtain the target MI-EEG signal.

14. The electronic device of claim 13, wherein preprocessing the initial source MI-EEG signal to obtain the source MI-EEG signal comprises:

intercepting a signal of a predetermined duration from the initial source MI-EEG signal to obtain a first source MI-EEG signal;

inputting the first source MI-EEG signal to a band-pass filter, to obtain a second source MI-EEG signal; and standardizing the second source MI-EEG signal to obtain the source MI-EEG signal.

15. The electronic device of claim 13, wherein preprocessing the initial target MI-EEG signal to obtain the target MI-EEG signal comprises:

intercepting a signal of a predetermined duration from the initial target MI-EEG signal to obtain a first target MI-EEG signal;

inputting the first target MI-EEG signal to a band-pass filter, to obtain a second target MI-EEG signal; and standardizing the second target MI-EEG signal to obtain the target MI-EEG signal.

16. The electronic device of claim 10, wherein before inputting the source MI-EEG signal belonging to the source domain and the target MI-EEG signal belonging to the target domain to the initial feature extraction model, the processor is configured to further cause the electronic device to perform steps, comprising:

transmitting a target instruction to a collection device, the target instruction being used for indicating the first known action to be performed; and receiving the source MI-EEG signal transmitted from the collection device, the source MI-EEG signal being an MI-EEG signal collected by the collection device within a particular time period after receiving the target instruction.

17. A non-transitory computer-readable storage medium, storing a computer program, the computer program, when executed by an electronic device, causing the electronic device to:

input a source MI-EEG signal belonging to a source domain and a target MI-EEG signal belonging to a target domain to an initial feature extraction model to obtain first source MI features representing the source MI-EEG signal and first target MI features representing the target MI-EEG signal;

input the first source MI features to an initial classification model to obtain a first classification result outputted by the initial classification model, the first classification result representing an action predicted to be performed in the source MI-EEG signal;

adjust, in response to a first known action corresponding to the source MI-EEG signal is inconsistent with the action predicted to be performed of the source MI-EEG signal, or a similarity between a feature distribution of the first source MI features and a feature distribution of the first target MI features is less than a first predetermined threshold, a model parameter of the initial feature extraction model and/or a model parameter of the initial classification model to obtain a target feature extraction model and a target classification model, wherein the adjusting is performed iteratively using the source MI-EEG signal and the target MI-EEG signal, and a similarity between a feature distribution of second source MI features representing the source MI-EEG signal and outputted by the target feature extraction model and a feature distribution of second target MI features representing the target MI-EEG signal and outputted by the target feature extraction model is greater than or equal to the first predetermined threshold, and an action predicted to be performed, represented by a second classification result outputted by the target classification model, of the source MI-EEG signal that is consistent with the first known action; and control, according to the second classification result, a target device to perform the action predicted to be performed.

18. The non-transitory computer-readable storage medium of claim 17, wherein the computer program, when executed by the electronic device, causes the electron device to adjust the model parameter of the initial feature extraction model and/or the model parameter of the initial classification model to obtain the target feature extraction model and the target classification model by:

inputting the first source MI features and the first target MI features to an initial domain discrimination model to obtain a first source discrimination result and a first target discrimination result, the initial domain discrimination model being used to:

determine, according to the feature distribution of the first source MI features, a probability that the source MI-EEG signal belongs to the source domain and a
probability that the source MI-EEG signal belongs to
the target domain, and determine, according to the feature distribution of the
first target MI features, a probability that the target
MI-EEG signal belongs to the source domain and a
probability that the target MI-EEG signal belongs to
the target domain; and adjusting the model parameter of the initial feature extrac-
tion model and/or the model parameter of the initial
classification model and a model parameter of the
initial domain discrimination model by using the
source MI-EEG signal and the target MI-EEG signal
via a plurality of iterations to obtain:

the target feature extraction model,
the target classification model, and
a target domain discrimination model, wherein a difference between the probability that the
source MI-EEG signal belongs to the source domain
and the probability that the source MI-EEG signal
belongs to the target domain that are determined by the
target domain discrimination model according to the
second source MI features being less than or equal to a
second predetermined threshold, and a difference between the probability that the target MI-
EEG signal belongs to the source domain and the
probability that the target MI-EEG signal belongs to the
target domain that are determined by the target domain
discrimination model according to the second target MI
features being less than or equal to the second prede-
termined threshold.

19. The non-transitory computer-readable storage
medium of claim 17, wherein when the target MI-EEG
signal corresponds to a second known action, the non-
transitory computer-readable storage medium is further
executed to cause the electronic device to perform steps,
comprising:

inputting the first target MI features to the initial classi-
fication model to obtain a third classification result
outputted by the initial classification model, the third
classification result representing an action predicted to
be performed in the target MI-EEG signal; and performing the step of adjusting the model parameter of
the initial feature extraction model and/or the model
parameter of the initial classification model when it is
determined that the first known action is inconsistent with the action
expected to be performed in the source MI-EEG signal,
or that the second known action is inconsistent with the
action predicted to be performed, represented by the
third classification result, of the target MI-EEG signal,
or that a similarity between the feature distribution of the
first source MI features and the feature distribution of
the first target MI features is less than the first prede-
termined threshold.

20. The non-transitory computer-readable storage
medium of claim 17, wherein before inputting the source
MI-EEG signal belonging to the source domain and the
target MI-EEG signal belonging to the target domain to the
initial feature extraction model, the non-transitory com-
puter-readable storage medium is further executed to cause
the electronic device to perform steps, comprising:

acquiring an initial source MI-EEG signal belonging to
the source domain and an initial target MI-EEG signal
belonging to the target domain;

preprocessing the initial source MI-EEG signal to obtain
the source MI-EEG signal; and preprocessing the initial target MI-EEG signal to obtain
the target MI-EEG signal.

* * * * *